(12) United States Patent
Thirstrup

(10) Patent No.: US 6,738,141 B1
(45) Date of Patent: May 18, 2004

(54) SURFACE PLASMON RESONANCE SENSOR

(75) Inventor: Carsten Thirstrup, Charlottenlund (DK)

(73) Assignee: Vir A/S, Taastrup (DK)

( * ) Notice: Subject to any disclaimer, the term of this patent is extended or adjusted under 35 U.S.C. 154(b) by 0 days.

(21) Appl. No.: 09/493,214

(22) Filed: Jan. 28, 2000

Related U.S. Application Data

(60) Provisional application No. 60/118,111, filed on Feb. 1, 1999.

(51) Int. Cl.⁷ .............................................. G01N 21/55
(52) U.S. Cl. ...................................................... 356/445
(58) Field of Search ................................ 356/445–446

(56) References Cited

U.S. PATENT DOCUMENTS

| 5,629,774 A | 5/1997 | Peacock et al. |
| 5,822,073 A | 10/1998 | Yee et al. |

FOREIGN PATENT DOCUMENTS

| EP | 0797090 A2 | 9/1997 |
| EP | 0797091 A1 | 9/1997 |
| EP | 0805347 A2 | 11/1997 |
| EP | 0 863 395 A2 | 9/1998 |
| WO | WO 90/05295 | 5/1990 |

*Primary Examiner*—Frank G. Font
*Assistant Examiner*—Amanda Merlino
(74) *Attorney, Agent, or Firm*—Harness Dickey

(57) ABSTRACT

Surface plasmon resonance (SPR) sensors comprise a sensor chip constructed of laterally integrated arrays of planar sensor chip units and an optical transducer constructed of laterally integrated arrays of planar optical transducer units. The replaceable sensor chip is separated from the optical transducer by a gap and perpendicular optical interconnections are between the sensor chip and the optical transducer. The optical interconnections between the sensor chip and the optical transducer are based on collimated light beams incident perpendicularly to the interfaces. Uncritical alignment of the optical transducer and the sensor chip is provided. The direction of the light beams will not be changed when passing through the interfaces between the sensor chip, the gap and the optical transducer eliminating the need of disposing refractive index matching gels in the gap.

49 Claims, 12 Drawing Sheets

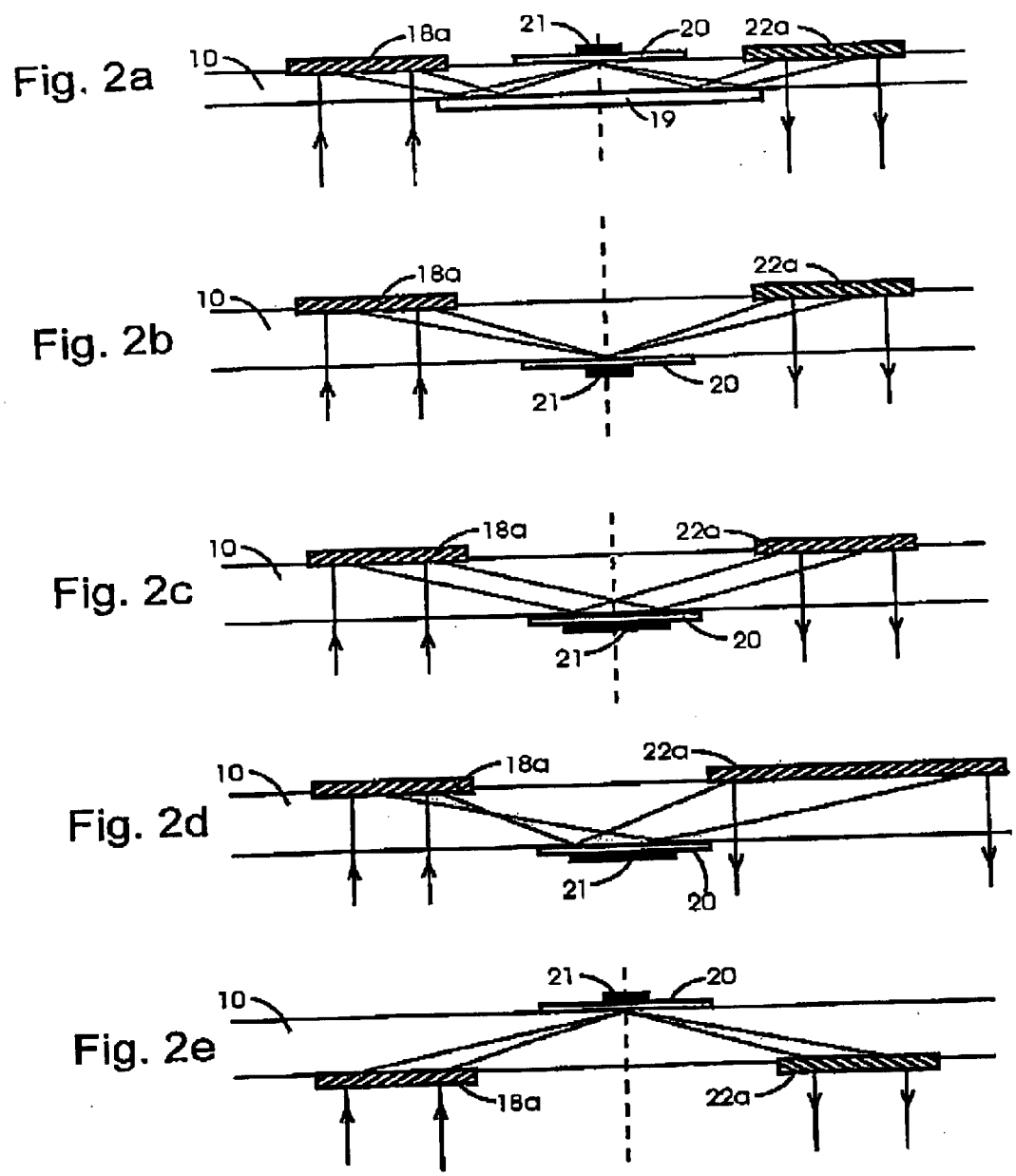

SURFACE PLASMON RESONANCE SENSOR

This application claims priority on provisional application No. 60/118,111 filed on Feb. 1, 1999, the entire contents of which are hereby incorporated by reference.

FIELD OF INVENTION

The present invention relates to surface plasmon resonance (SPM) sensors. More particularly, the present invention relates to the field of water quality monitoring, where there is a need for sensors being able to measure a large amount of different compounds having the potential of polluting our water resources. Other possible applications are food quality monitoring, process control, biological components including human immunodeficiency virus (HIV) core protein detection and in gene expression monitoring.

BACKGROUND OF THE INVENTION

Surface plasmons (SPs) are normal modes of charge density that exists at the interface between a dielectric and a metal/semiconductor. It was discovered 30 years ago that the coupling between SPs and the electromagnetic field of light is sensitive to the changes in the optical properties of the dielectric medium close to a metal surface. SPR sensors have attracted attention primarily for medical and environmental applications.

Monitoring of different analytes may be determined by an array of different molecular recognition elements (MREs), each element having a specific response to a particular analyte. The MREs can be biological, biochemical or chemical recognition elements or a combination of these elements.

MREs can for example be immobilized directly on the surface of a metal film supporting SP waves at resonance with the light (SPR metal film), e.g. through thiols binding to a gold surface.

Alternatively, the MREs can be immobilized for example through covalent binding in a suitable polymer film (e.g. hydrogel) that is a few hundred nanometers thick coating the SPR metal film. Depending on applications, various sensing schemes of MREs have been reported including antibody-antigen reactions, arrays of oligonucleotides or probes originating from cDNA libraries for DNA hybridization analysis, molecular imprinting techniques, ionic interaction with ionophores and chromo-ionophores, and electrochemical interaction where the SPR metal film acts as one of the two electrodes (the cathode or the anode). Although these MREs are very different in nature, they have the inherent property that they all make use of surface or interface sensitive bio-/chemical interactions, and these interactions can quantitatively be monitored using a SPR sensing scheme.

Since SPs propagate in the transverse magnetic mode (TM mode), optical excitation is only possible in cases where the electric field is polarized parallel to the incident plane (TM polarization) and the wave vectors of the light and the SP are matched. The wave vector $k_{SP}$ of the SP at the metal/dielectric interface (i.e. the interface between the metal and the sample to be measured) and at a wavelength $\lambda$ is given approximately by:

$$k_{SP} \sim \frac{2\pi}{\lambda} \sqrt{\frac{\varepsilon_m \varepsilon_s}{\varepsilon_m + \varepsilon_s}} \qquad (1)$$

where $\varepsilon_s$ and $\varepsilon_m$ are the real parts of the dielectric constants of the sample and the metal, respectively. The incident light cannot couple directly to SPs on smooth surfaces, since for negative values of $\varepsilon_m$ as is the case for metals, the wavevector for the light and the SP can never be matched. SPs can be excited either electronically, optically using a grating or optically using coupling of evanescent waves of light to a metal surface. The latter approach is often performed using the Kretschmann configuration, which consists of a thin metal film coating one face of a high index prism ($n_p \sim 1.4$–$1.7$).

Light passing through the prism increases momentum and is totally reflected from the metal surface at an angle $\theta$, which is greater than the critical angle between the prism and the sample. The component of the wave vector of light $k_{ev}$, being parallel to the metal/dielectric interface and incident on the metal surface with a wavelength $\lambda$, is given by:

$$k_{ev} \sim \frac{2\pi}{\lambda} \sqrt{\varepsilon_g} \sin\theta \qquad (2)$$

where $\varepsilon_g$ is the dielectric constant of the prism. The parameters $\varepsilon_m$ and $\varepsilon_g$ are usually fixed and $\varepsilon_s$ is the dielectric constant of the sensing area to be measured and its value changes according to the analyte detection. At wave vector matching, $k_{SP} = k_{ev}$, the light interacts strongly with the SP giving rise to a large decrease in the reflectivity of the light from the metal/dielectric interface. This condition characterizes the SPR and can be measured using various methods including focusing a beam with an angular band of the light covering the SPR angle, scanning the wavelength of the incident light or a combination of both methods.

A commercial SPR system from the company BIAcore is based on a Kretchmann configuration, but where the SPR metal film is disposed on a replaceable glass plate which is physically separated from a glass prism by means of a refractive index matching gel disposed in between the glass prism and the glass plate. This instrument is large and expensive and there has been much effort in the art to provide small and compact SPR sensors.

U.S. Pat. No. 5,629,774 describes a portable SPR sensor with the object of measuring analyte in a fluid. The sensor comprises a monochromatic light source, a surface plasmon resonance-sensitive device for reflecting the light and a detector based on one or more photo-detectors combined with an "opening" such as a pin hole. The "opening" defines a particular angle on the critical side of the SPR resonance minimum. Small changes in the sample produces large changes in the reflected intensity monitored by the light detector. Compared to systems employing a scanning mechanism or using a focusing light beam with an angular band of light covering the SPR angle, a disadvantage of the system described in U.S. Pat. No. 5,629,774 is related to the use of a single detector which requires a more precise alignment of the system.

In EP 0 797 090, all mirrors, the sensing layer, the photo-detector array and optionally the light source are integrated in the same house. A disadvantage of this configuration is the fact that all components have to be replaced when replacing the sensing layer.

Optional configurations have been described in EP 0 797 091, where a transparent base housing and a detachable prism-like optical housing are index matched to avoid undesirable refraction of the light rays. This is performed using index matching gel between the base housing and the optical housing or fabricating concave portions in the base housing and complementary convex portions in the optical housing at the intersections between the two housings. Both options seem to be complicated solutions for practical working SPR sensors.

It is a disadvantage of the above-mentioned systems that these systems apply an index matching gel. The gel is inconvenient to work with and it may cause problems if comes in contact with some of the optical or bio-/chemical elements.

EP 0 805 347 describes a surface plasmon sensor where the metal layer supporting the surface plasmons is positioned on a glass substrate. An incoming optical light beam is directed towards the metal layer using a first transmission grating. The incoming optical light beam is also focussed by the first transmission grating. The directed optical light beam is reflected off the metal layer and propagates towards a second transmission grating. The second transmission grating directs the transmitted beam towards a detector.

It is a disadvantage of the sensor described in EP 0 805 347 that the incoming light beam is incident under angle that differs from normal incidence.

Generally in the prior art, the SPR sensing layers, the light sources, the mirrors and the detectors have been arranged in three-dimensional configurations where at least one component is aligned at an angle close to the SPR angle (~50°–80°) compared to the other components. This implies that integration of sensors with large arrays of sensing areas cannot be readily made. Integration shall preferably be carried out laterally, which requires a planar configuration of layers or planar configurations aligned parallel to each other Therefore, there is a need in the prior art of compact SPR sensors comprising dispensable sensor chips with a large array of sensing areas, with uncritical alignment between sensor chips and optical transducers, and with no requirements of using index matching gels.

It is an object of the present invention to provide a SPR sensor comprising a sensor chip constructed of laterally integrated arrays of planar sensor chip units (SCU)

It is a further object of the present invention to provide a SPR sensor comprising an optical transducer constructed of laterally integrated arrays of planar optical transducer units.

It is a still further object of the present invention to provide a SPR sensor comprising two separable units—a sensor unit and a transducer unit.

It is a still further object of the present invention to provide a SPR sensor with uncritical alignment between the sensor unit and the transducer unit.

It is a still further object of the present invention to provide a SPR sensor wherein the use of index matching gel is avoided.

SUMMARY OF THE INVENTION

The above-mentioned objects are complied with by providing, in a first aspect, a surface plasmon resonance sensor comprising a first unit and a second unit, said first and second units being separable, and wherein said first unit comprises:
a first housing,
a film of electrically conducting material being adapted to support surface plasmons, said film being hold by a first exterior surface part of the first housing,
optical input means positioned on a second exterior surface part of the first housing so as to receive an optical light beam from the second unit,
optical output means positioned on a third exterior surface part of the first housing so as to transmit an optical light beam to the second unit,
a first set of optical elements being adapted to direct the received optical light beam from the first unit towards the electrically conducting film,
a second set of optical elements being adapted to direct an optical light beam from the electrically conducting film towards the optical output means so as to transmit the optical light beam from the electrically conducting film to the second unit,
and wherein said second unit comprises:
a second housing,
means for emitting an optical light beam,
a first set of optical elements being adapted to prepare the emitted optical light beam,
optical output means positioned on a first exterior surface part of the second housing so as to transmit the prepared optical light beam to the first unit,
optical input means positioned on a second exterior surface part of the second housing so as to receive an optical light beam from the first unit,
detecting means being adapted to detect the optical light beam received from the first unit,
a second set of optical elements being adapted to direct the received optical light beam from the first unit towards the detecting means,
wherein the propagation directions of the optical light beams at the positions of the optical input and optical output means are essentially perpendicular to the exterior surface parts of the first and the second housing so as to avoid refraction of the optical light beams upon entry of said optical light beams into the first and second unit.

In this and the following aspects of the present invention essentially perpendicular means that the angle of incidence may be in the range −10°–10°, preferably in the range −5°–5°, more preferably in the range −2°–2° and even more preferably in the range −0.5°–0.5°.

The emitting means may comprise a laser source, such as a semiconductor laser diode. The light emitting means may emit light at essentially a single wavelength. Alternatively, the light emitting means may emit light at a plurality of wavelengths using e.g. a light emitting diode.

The first set of optical elements of the second unit may comprise means for collimating the emitted optical light beam. The collimating means may comprise lens means.

By collimated—as mentioned here and in some of the following aspects—is meant that the angular beam spread of the emitted optical light beam may be less than 10°, preferably less than 5°, more preferably less than 2° and even more preferably less than 0.5°.

The first set of optical elements of the second unit may further comprise means for polarizing the emitted optical light beam. This polarizing means may be any kind of polarizing film, prism arrangement or voltage controlled variable retarder.

The input and output means of the first and second units may comprise antireflecting coatings.

The detecting means may comprise an array of photosensitive elements, such as a multiple photo detector array, a charge coupled device or a complementary metal oxide semiconductor image sensor. The sensor may further comprise a light shield member.

The first set of optical elements of the first unit may comprise a diffractive member, such as a diffractive grating or a holographic grating. In a similar way, the second set of optical elements of the first unit may comprise a diffractive member, such as a diffractive grating or a holographic grating. The diffractive members may be formed by reflective members. The second set of optical elements may also comprise a reflective member, such as a reflective mirror.

The electrically conducting film may comprise a metal film, such as a gold film, a silver film, an aluminum film or a titanium film. The electrically conducting film may be formed by a plurality of electrically conducting films, said plurality of films being arranged in a laterally extending pattern.

To support long range surface plasmon resonances a layer of dielectric material may be positioned between the electrically conducting film and the first exterior surface part of the first housing. In case the surface plasmon resonance sensor comprises a plurality of electrically conducting layers the sensor may further comprise a layer of dielectric material being positioned between each of the plurality of electrically conducting films and the first exterior surface part of the first housing.

The surface plasmon resonance sensor may further comprise moving means being adapted to move the first and second unit relative to each other so as to move the focus point of an optical light beam relative to an electrically conducting film. Alternatively or in addition, the surface plasmon resonance sensor may comprise moving means being adapted to move the first and second unit relative to each other so as to vary the angle of incidence of an optical light beam directed towards an electrically conducting film.

The surface plasmon resonance sensor may comprise two or more surface plasmon resonance sensors preferably being arranged in a lateral extending pattern.

In a second aspect, the present invention relates to a method of determining the bio-/chemical composition of a sample using a surface plasmon resonance sensor, said surface plasmon resonance sensor comprising a first unit and a second unit, said first and second units being separable, and wherein said first unit comprises:
 a first housing,
 a film of electrically conducting material being adapted to support surface plasmons, said film being hold by a first exterior surface part of the first housing,
 optical input means positioned on a second exterior surface part of the first housing so as to receive an optical light beam from the second unit,
 optical output means positioned on a third exterior surface part of the first housing so as to transmit an optical light beam to the second unit,
 a first set of optical elements being adapted to direct the received optical light beam from the first unit towards the electrically conducting film,
 a second set of optical elements being adapted to direct an optical light beam from the electrically conducting film towards the optical output means so as to transmit the optical light beam from the electrically conducting film to the second unit,
and wherein said second unit comprises:
 a second housing,
 means for emitting an optical light beam,
 a first set of optical elements being adapted to prepare the emitted optical light beam,
 optical output means positioned on a first exterior surface part of the second housing so as to transmit the prepared optical light beam to the first unit,
 optical input means positioned on a second exterior surface part of the second housing so as to receive an optical light beam from the first unit,
 detecting means being adapted to detect the optical light beam received from the first unit,
 a second set of optical elements being adapted to direct the received optical light beam from the first unit towards the detecting means,
 wherein the propagation directions of the optical light beams at the positions of the optical input and optical output means are essentially perpendicular to the exterior surface parts of the first and the second housing so as to avoid refraction of the optical light beams upon entry of said optical light beams into the first and second unit.

In a third aspect, the present invention relates to a surface plasmon resonance sensor comprising a first unit, said first unit comprising:
 a first housing,
 a layer of electrically conducting material being adapted to support surface plasmons, said layer being held by a first exterior surface part of the first housing,
 optical input means positioned on a second exterior surface part of the first housing, said optical input means being adapted to receive an optical light beam,
 optical output means positioned on a third exterior surface part of the first housing, said optical output means being adapted to transmit an optical light beam,
 a first diffractive optical element being adapted to direct the received optical light beam towards the electrically conducting layer,
 a second diffractive optical element being adapted to direct a reflected optical light beam from the electrically conducting layer towards the optical output means,
 wherein the propagation directions of the optical light beams at the positions of the optical input and optical output means are essentially perpendicular to the exterior surface parts of the first housing so as to avoid refraction of the optical light beams at the positions of the optical input and optical output means.

The surface plasmon resonance sensor according to the third aspect may further comprise a second unit, said second unit comprising:
 a second housing,
 means for emitting an optical light beam,
 a set of optical elements being adapted to prepare the emitted optical light beam,
 optical output means positioned on a first exterior surface part of the second housing, said optical output means being adapted to transmit the prepared optical light beam to the first unit,
 optical input means positioned on a second exterior surface part of the second housing, said optical input means being adapted to receive an optical light beam from the first unit,
 detecting means being adapted to detect the received optical light beam from the first unit,
 wherein the propagation directions of the optical light beams at the positions of the optical input and optical output means are essentially perpendicular to the exterior surface parts of the second housing so as to avoid refraction of the optical light beams at the positions of the optical input and optical output means.

The second unit may further comprise an optical element being adapted to direct the received optical light beam from the first unit towards the detecting means.

The light emitting means may comprise light sources as described in relation to the first aspect of the present invention. The set of optical elements of the second unit may comprise collimating and/or polarizing means as described in accordance with the first aspect of the present invention.

The input and output means of the first and second units may be coated with an antireflecting coating.

As with the first aspect of the present invention, the detecting means may comprise an array of photosensitive elements, such as a multiple photo detector array, a charge coupled device or a complementary metal oxide semiconductor image sensor. The first and second diffractive optical element of the first unit may comprise an optical grating, such as a reflective holographic grating.

In a fourth aspect, the present invention relates to a surface plasmon resonance sensor comprising:

a transparent member, a layer of electrically conducting material being adapted to support surface plasmons, said layer being held by an exterior surface part of the member, a first optical grating being held by a first exterior surface part of the member and being adapted to direct a received optical light beam towards the electrically conducting layer, wherein the propagation direction of the received optical light beam at the position of the first optical grating is essentially perpendicular to the first exterior surface part of the member and wherein the received optical light beam is collimated, and a second optical grating being held by a second exterior surface part of the member and being adapted to receive an optical light beam from the electrically conducting layer and being adapted to re-emit the optical light beam received from the electrically conducting layer, wherein the propagation direction of the re-emitted optical light beam at the position of the second optical grating is essentially perpendicular to the second exterior surface part of the member and wherein the re-emitted optical light beam is collimated.

The surface plasmon resonance sensor according to the fourth aspect may further comprise means for emitting an optical light beam, a set of optical elements being adapted to prepare the emitted optical light beam, and means for detecting the re-emitted optical light beam.

Even further, the surface plasmon resonance sensor according to the fourth aspect may comprise an optical element being adapted to direct the re-emitted optical light beam towards the detecting means.

The light emitting means may comprise light sources as described in relation to the first and third aspect of the present invention. The set of optical elements of the second unit may comprise collimating and/or polarizing means.

The detecting means may comprise an array of photosensitive elements, such as a multiple photo detector array, a charge coupled device or a complementary metal oxide semiconductor image sensor.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2 illustrates schematically cross sections of sensor chip units (SCUs) for 5 different configurations (a–e) in the present invention.

DETAILED DESCRIPTION OF THE INVENTION

Figure 1:
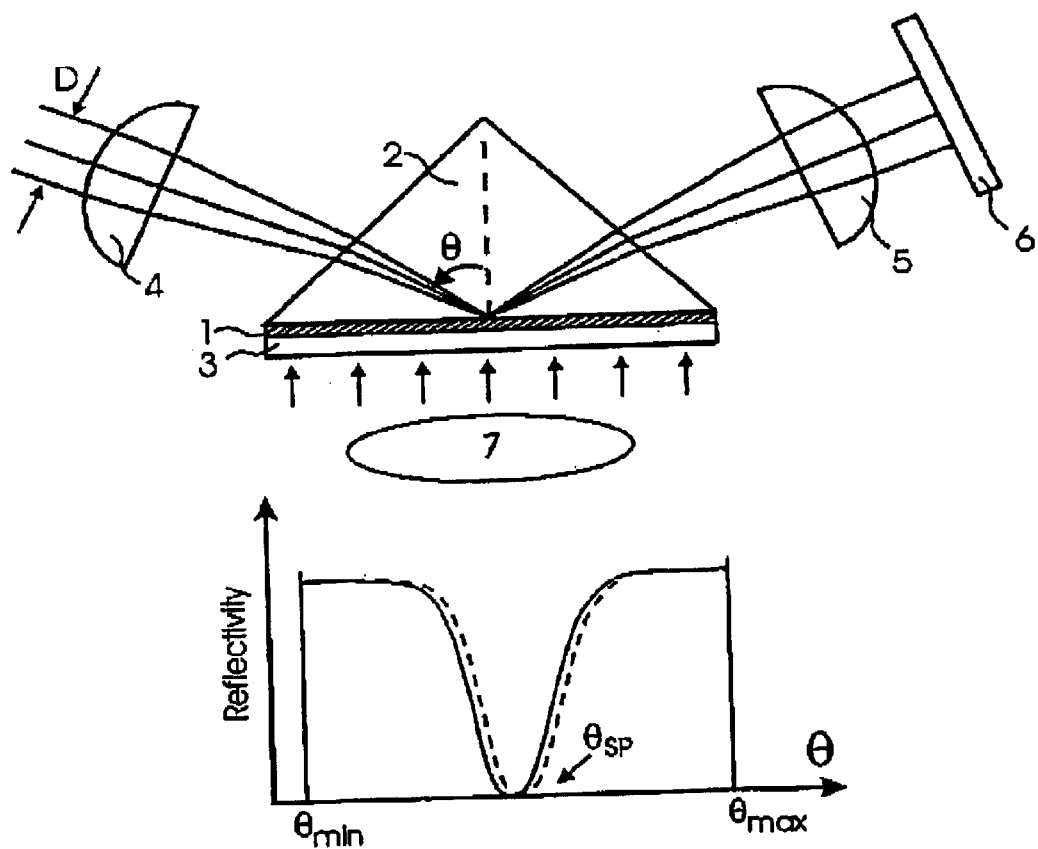
FIG. 1 is a schematic illustration of a conventional surface plasmon resonance sensor based on the Kretschman configuration and a corresponding plot of the reflectivity of the light reflected from the surface plasmon sensing area as a function of angle of incidence. Plots are depicted for the case of no analyte response (solid curve) and for the case of analyte response (dashed curve).

FIG. 1 illustrates a conventional Kretschmann configuration of a SPR sensor consisting of a high index prism (2), a thin metal film (1) coating on one side of the prism and a bio-/chemical sensing thin film area (3) covering the metal film. Employing a lens (4), collimated monochromatic light is focused onto the metal film through the prism (2). The light beam has a certain beam width D, and a range of angular bands θ varying from $\theta_{min}$ to $\theta_{max}$ are incident on the metal film. Another lens (5) images the light beam reflected from the metal film onto a detector array (6). The range of θ is matched to cover the SPR angle $\theta_{SP}$, which is determined as a minimum in the reflectivity of light by the detector array (6). When changes in the ambient conditions (7) occur, the layer thickness and/or the refractive index of the bio-/chemical sensing area (3) are changed. This gives rise to a change in the SPR response by a displacement in the position of $\theta_{SP}$ as illustrated schematically in FIG. 1, where the solid SPR curve moves to the position of the dashed SPR curve.

The present invention incorporates the measurement principle based on imaging a range of angular bands or a range of wavelengths onto a single detector array. All components in the present invention are either available commercially or can be made using state of the art fabrication techniques. The SPR sensor comprises a combination of:

1) a replaceable sensor chip constructed of laterally integrated arrays of planar sensor chip units (SCUs), and
2) an optical transducer constructed of laterally integrated arrays of planar optical transducer units (OTUs).

Five different configurations of sensor chip units (SCUs) of the present invention are illustrated in FIGS. 2(a–e). Via a first set of optical elements (18a), a collimated light beam entering the SCU perpendicularly to the backside surface of the SCU is directed towards a SPR film (20) being disposed on the topside surface of the SCU and underneath one or more sensing areas (21). Via a second set of optical elements (22a) the light beam being reflected from the SPR metal film is collimated and exits the SCU perpendicular to the backside surface of the SCU.

In FIG. 2(a), the first set of optical elements, the SPR metal film and the second set of optical elements are disposed on the topside of the SCU and a reflective mirror is disposed on the backside surface of the SCU. In FIGS. 2(b)–(d), the first set of optical elements and the second set of optical elements are disposed on the topside of the SCU, and the SPR metal film is disposed on the backside of the SCU. In FIG. 2(e), the first set of optical elements and the second set of optical elements are disposed on the backside surface of the SCU, and the SPR metal film is disposed on the topside of the SCU. The present invention covers configurations, where the light beam propagating in the SCU is either focused on the SPR metal film as in FIGS. 2(a), (b) and (e), or the light beam propagating in the SCU is focused in between the first set of optical elements and the second set of optical elements as in FIG. 2(d), or the light beam propagating in the SCU is collimated as in FIG. 2(c). For the configurations in FIGS. 2(a–d), the first and the second set of optical elements are mirrors (cylindrical parabolic mirrors) or reflective diffractive optical elements (RDOE). For the configuration in FIG. 2(e), the first and the second set of optical elements are lenses, microlens arrays or transmission diffractive optical elements.

Figure 3A:
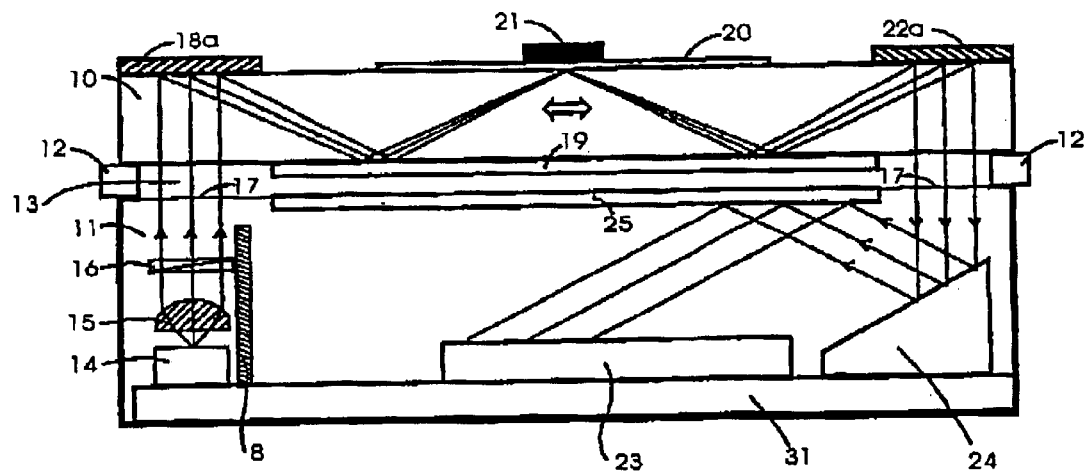
FIG. 3 is a schematic cross sectional illustration of a sensor chip unit and the corresponding optical transducer unit separated by a gap in the preferred embodiment of the present invention based on a substantially monochromatic light source and coupling of the light at angular bands covering the SPR angle. In a), the sensor chip unit is depicted for a SPR angle of ~60° and in b), the sensor chip unit is depicted for a SPR angle of ~75°. Light rays originating from the light source are plotted as solid lines.
Figure 3B:
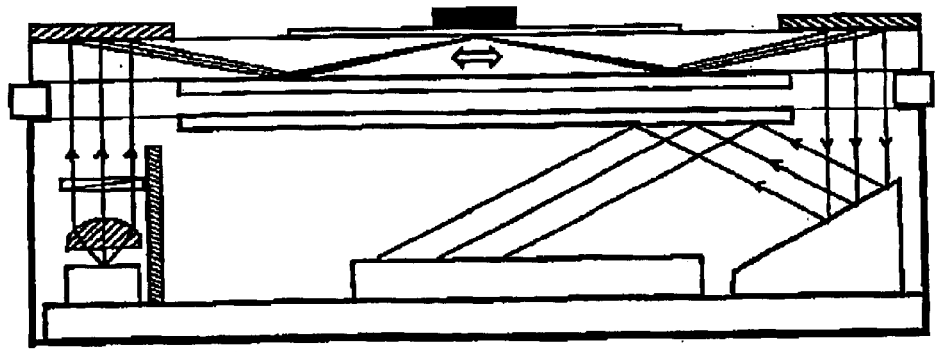

FIG. 3 depicts a first and a preferred embodiment of the present invention, where the SCU as depicted in FIG. 2(a) and an optical transducer unit (OTU) (11) are separated by means of a support frame (12), which leaves a gap (13) between the two units.

A light beam from a monochromatic light source (14) mounted in a base plane (31) is collimated by a lens or a lens system (15) and polarized by a polarizer (16). The light beam passes through a transparent separation plane (17) and enters the SCU (10) perpendicularly to the backside surface of the SCU. A light shield (8) shields the detector array from stray light emerging from the light source (14) and prevents interference between light emitted from the light source (14) and light reflected from the surface of the detector (23). Inside the SCU, the light beam is reflected from a reflective diffractive optical element (RDOE) (18a) transforming the light beam into a cylindrically focusing light beam. Via a flat reflective mirror (19) disposed on the backside surface of the SCU, the light beam is subsequently reflected and focused onto a line on a SPR metal film (20) underneath one or more sensing areas (21) on the top. The focused light beam comprises angular bands covering the SPR angle. After being reflected from the SPR metal film (20), the light beam is reflected from the flat mirror (19). Via a second RDOE (22a), it is transformed into a collimated light beam again, which exits the SCU perpendicularly to the backside surface of the SCU and reenters the OTU perpendicularly to the transparent separation plane (17). A flat mirror (24) mounted in the base plane combined with a flat mirror (25) mounted in the center of the transparent separation plane images the collimated light beam onto a detector array (23). Alternatively, the mirrors (24) and (25) can be omitted or they can be replaced by other optical means such as a lens system.

Typically, the gap between the SCU (10) and the OTU (11) is filled with atmospheric air and since the refractive index of the substrate material of the SCU is ~1.6, the internal critical angle for total reflection $\theta_c$~39°. This is lower than $\theta_{SP}$ and the flat mirror on the backside surface can therefore simply be the natural reflection of the light beam from the air/substrate interface. In applications where the sensor is immerged in water and the water fills the gap, $\theta_c$ is close to $\theta_{SP}$ and a metallic mirror may be needed on the backside surface of the SCU.

The optical interconnections between the sensor chips and the optical transducers are based on collimated light beams propagating perpendicularly to the planar interfaces between the optical transducer, the gap and the sensor chip. The direction of the light beam will therefore not be changed when passing through the planar interfaces. As a result, the vertical alignments of the SCUs and OTUs are uncritical and the operation of the sensor is insensitive to the magnitude of the refractive index of the gap eliminating the need of index matching gels.

In addition, the combination of using focusing and collimating optics integrated in the sensor chip and large light beam diameters covering a sufficiently large angular band ensures an uncritical alignment in the horizontal direction. The partial reflections from the interfaces, which is ~4% in the case of air/plastic or air/glass, is reduced to ~0.5% by incorporating antireflection coatings on the planar interfaces. Possible antireflection coating materials are $MgF_2$ and $AlF_3*MgF_2$.

As illustrated by the two configurations of SCUs in FIG. 3, where in a) the SPR angle is ~60° and in b) the SPR angle is ~75°, sensor chips with different ranges of SPR angles can be used for the same optical transducer. The lateral integration of planar sensor chip units and planar optical transducer units provides means of integrating a number of sensing areas (21) on the same sensor chip. Each sensing area (21) typically comprises a polymer membrane with immobilized molecular recognition elements (MREs) responding specifically to a particular analyte. Fabrication methods for arrays of polymer membranes include ink jet printing techniques and micromachined microdispensers.

In the configuration as illustrated in FIG. 3, the mirrors (24) and (25) are flat and the width of the light beam impinging on the detector array will be kept unchanged. Since the angle of incidence in this case is larger than 0° and typically, between 20° and 45°, the area on the detector array illuminated by the light beam will be larger than the cross sectional area of the light beam. The resolution of the SPR measurement is increased, but the response of the detector array will fall off compared to a configuration without the mirrors (24) and (25) and where the light beam impinges with 0° angle of incidence on the detector array. Since the light intensity from the light source can be sufficiently large, the fall off of the response of the detector array is not considered to be a major problem with the present configuration.

The resolution of the detector array can be further improved by replacing one or both of the flat mirrors (24) and (25) by a system comprising at least one convex mirror, a convex lens or a diffractive optical element having the function of diverging the light beam passing through the separation plane (17) and increasing the area on the detector array illuminated by the light beam.

The light source can be a laser diode including a surface emitting laser diode, a light emitting diode (LED) or any other monochromatic light source. Examples are the Hitachi HI-L520RNC light emitting diode emitting at 700 nm, the Toshiba TOLD9221M InGaAlP multiple quantum well laser diode emitting at 670 nm, the Mitsubishi ML40123N AlGaAs multiple quantum well laser diode emitting at 780 nm or the Honeywell GaAs vertical cavity surface emitting laser diode SV2637-001 emitting at 850 nm, The lens (15) is an aspheric lens or a lens system, which collimates the light beam emitted from the light source (14). The lenses are made of a transparent material for the light beam, e.g. glass or plastic. The polarizer can be a passive optical component with a fixed direction of polarization or a voltage controlled variable retarder comprising e.g. a liquid crystal or a $LiNbO_3$ crystal. Light emitted from a laser diode normally has a well defined polarization, but the light from a LED is normally not well defined and a polarizer can be used to optimize the visibility in the SPR response.

The choice of the detector array (23) is determined by the size of the sensor and the resolution required. It may consist of multiple photodiode arrays (e.g. a Hamamatsu S3921-128Q, F with an array of 128 pixels), charge coupled device arrays (e.g. a SONY ICX059CL with an array of 795×596 pixels) or a complementary metal oxide semiconductor image sensor (e.g. Vision VV5404 integrated 356×292 pixel monochrome CMOS image sensor).

Figure 4A:
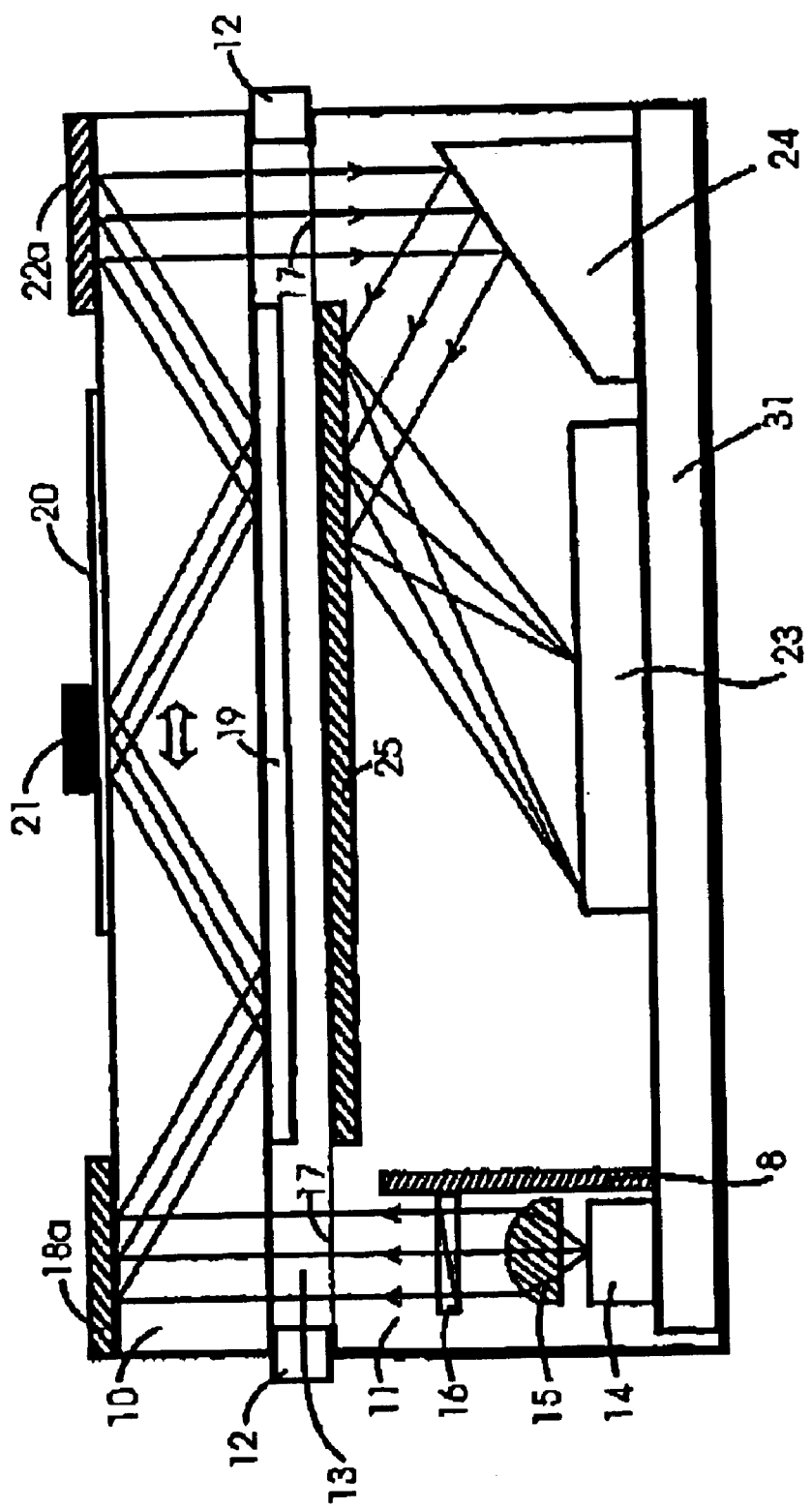
FIG. 4 illustrates two other embodiments of the present invention, each with a sensor chip unit and the corresponding optical transducer unit separated by a gap. The configuration in FIG. 4(a) is based on a polychromatic light source, a fixed coupling angle and with a grating in the optical transducer unit that enables measurements of the spectral band of the light. Light rays originating from the light source are plotted as solid lines. The configuration in FIG. 4(b) is based on a monochromatic light source and coupling of the light at angular bands covering the SPR angle. Light rays originating from the first light source are plotted as solid lines and light rays originating from the second light source are plotted as dashed lines.

FIG. 4 illustrates two other embodiments of the present invention, each with a SCU and the corresponding OTU separated by a gap. The second embodiment of the invention in FIG. 4(a) comprises a SCU as depicted in FIG. 2(c), but with an additional reflective mirror disposed on the backside surface of the SCU, and an OTU where the light source (14) is a white light source (e.g. a white LED lamp from Nichia Chemical Industries, Ltd). The flat mirror (25) according to the first embodiment of the invention has been replaced by a diffraction grating or a holographic grating. The SPR angle is kept constant and the detector array (23) measures the wavelength of light corresponding to wave vector matching of the light and the SP. The grating (25) diffracts the light and images the light on different pixels in the detector array according to the wavelength of light. The RDOEs (18a) and (22a) are now designed to exhibit minimum wavelength dependent deflection angle and they reflect the collimated light beam into a collimated light beam inside the sensor chip unit.

Figure 4B:
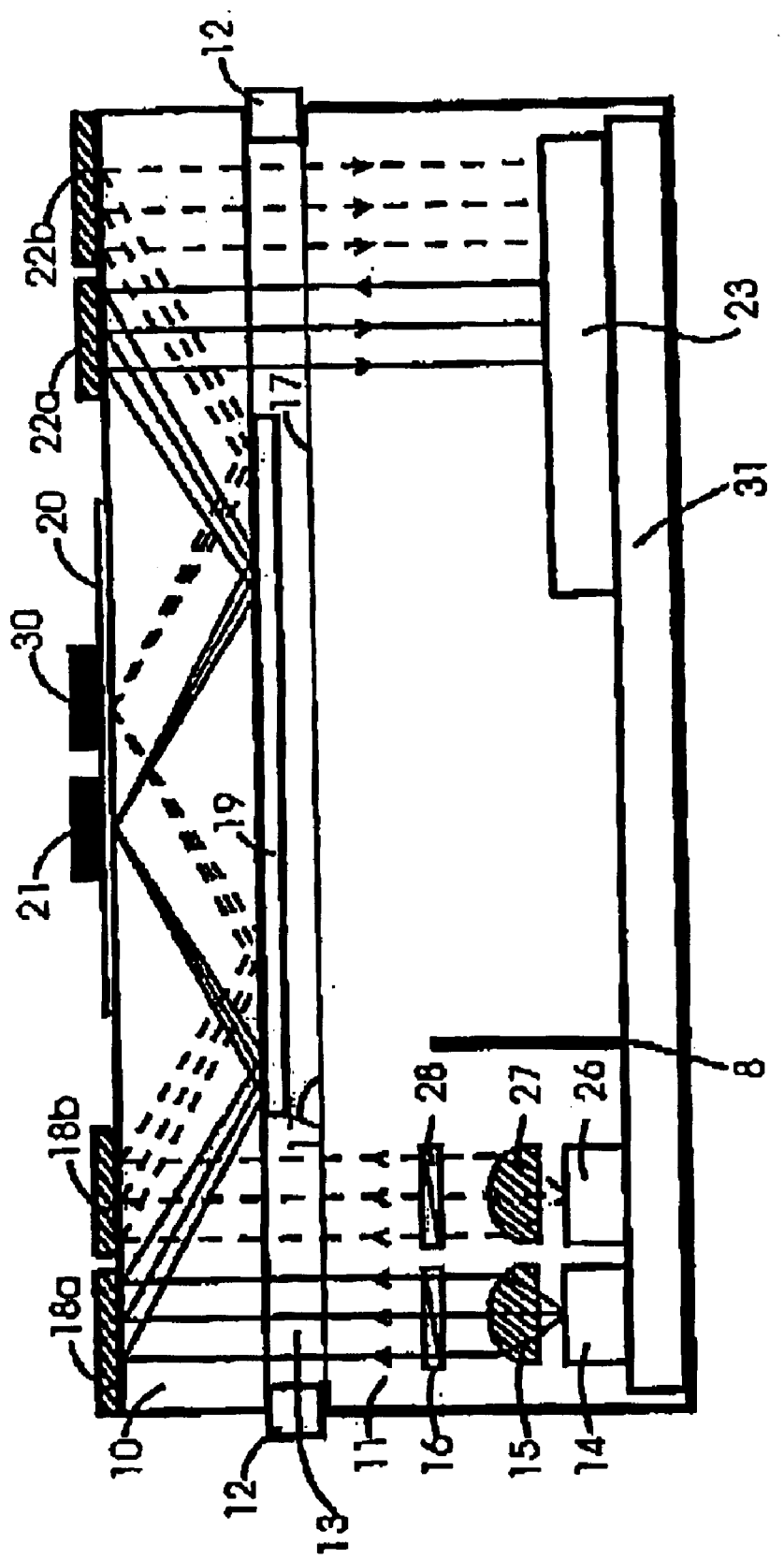

FIG. 4(b) illustrates a third embodiment of the present invention. The third embodiment of the present invention comprises the same components as the first embodiment of the present invention (see FIG. 3), but the plane mirrors (24) and (25) have been omitted, and the third embodiment further comprises a second monochromatic light source (26) mounted in the base plane (31), which radiates a second light beam. The second light beam is collimated by a second lens or second lens system (27), polarized by a second polarizer (28), passes through the transparent separation plane (17) and enters the SCU (10) perpendicularly to the backside surface of the SCU. Alternatively, the first and the second light beam originate from the same monochromatic light source and the lens system is designed in a manner to create a collimated light beam comprising both the first light beam and the second light beam.

Inside the SCU, the second light beam is reflected from a third RDOE (18b) transforming the second light beam into a cylindrically focusing second light beam. Via the flat mirror (19), the second light beam is reflected and focused onto a line on the SPR metal film (20) underneath one or more sensing areas (30). The focused second light beam comprises angular bands covering the SPR angle.

After being reflected from the SPR metal film (20), the second light beam is reflected from the flat mirror (19) and via a fourth RDOE (22b), it is transformed into a collimated second light beam, which exits the SCU (10) perpendicularly to the backside surface of the SCU. The second light beam further reenters the OTU (11) perpendicularly to the transparent separation plane (17) and it is imaged onto the detector array (23).

FIG. 5 illustrates the construction of SPR sensors from the SCUs and OTUs as shown in FIG. 4(b). A schematic top view of one SCU is illustrated in FIG. 5(a) with the four sensing elements (21a), (21b), (30a) and (30b), the metal film (20) and the RDOEs (18a), (18b), (22a) and (22b).

Figure 5A:
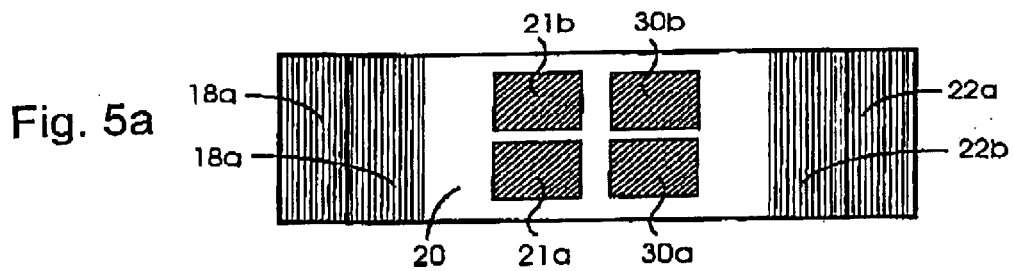
FIG. 5 are schematic top view illustrations of the embodiment of the present invention from FIG. 4(a) comprising a) a sensor chip unit and b) an optical transducer unit. In c) and d), an array of two sensor chip units and two optical transducer units are illustrated, respectively; and in (e) and the (f), an array of four sensor chip units and four optical transducer units are illustrated, respectively.
Figure 5B:
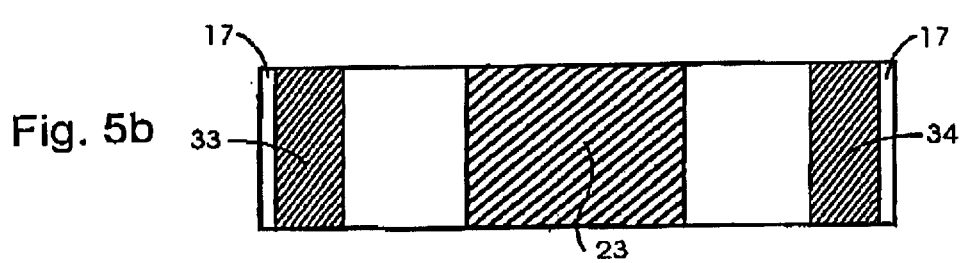
Figure 5C:
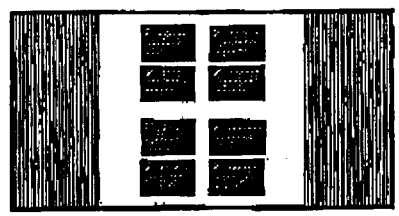
Figure 5D:
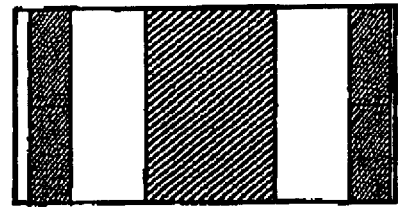
Figure 5E:
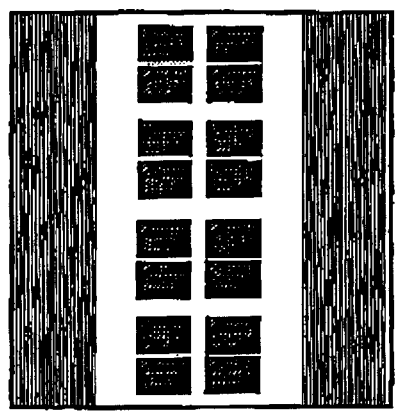
Figure 5F:
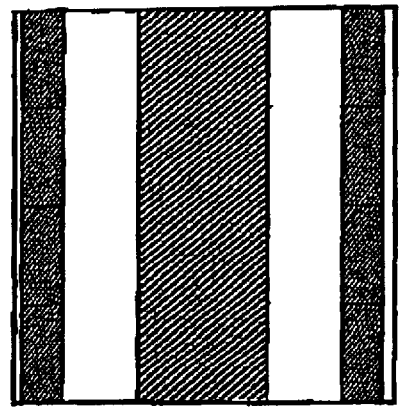

FIG. 5(b) shows a top-view of the corresponding OTU including the transparent separation plane (17), the detector array (23), the component (33) comprises the light sources, the lens systems and the polarizers. FIGS. 5(c) and 5(d) illustrate a sensor configuration comprising an array of two SCUs and the corresponding OTUs, and FIGS. 5(e) and 5(f) illustrate a sensor configuration comprising an array of four SCUs and the corresponding OTUs.

The principle of constructing sensors from SCUs and OTUs can be extended to N units where N is an integer number, which can be as large as desirable. The SCUs and the OTUs can either be arranged in an array aligned in the direction parallel to the RDOEs (the top-down direction in FIG. 5) or by extending the spatial dimension of each component in this direction. The sensor can alternatively be extended combining SCUs and OTUs in the direction perpendicular to the RDOEs (the left-right direction in FIG. 5). When operating the sensor, the sensor chip should be mounted on the top of the optical transducer. A sample comprising the analyte usually being dissolved in water is deposited on the top of the sensing areas. This is performed either using a dispenser or incorporating the sensing areas in a flow-injection cell.

Figure 6:
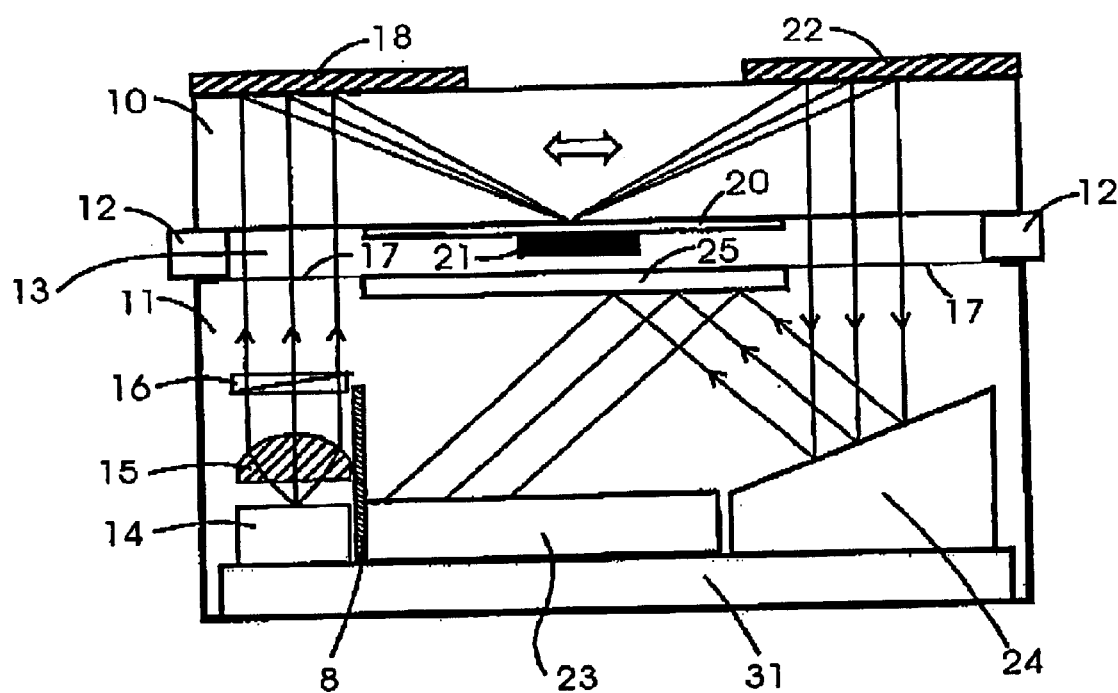
FIG. 6 is a schematic cross sectional illustration of a sensor chip unit and the corresponding optical transducer unit separated by a gap in the fourth embodiment of the present invention based on a monochromatic light source and coupling of the light at angular bands covering the SPR angle. In this configuration, the sensing areas are positioned on the backside surface of the sensor chip unit.
Figure 7A:
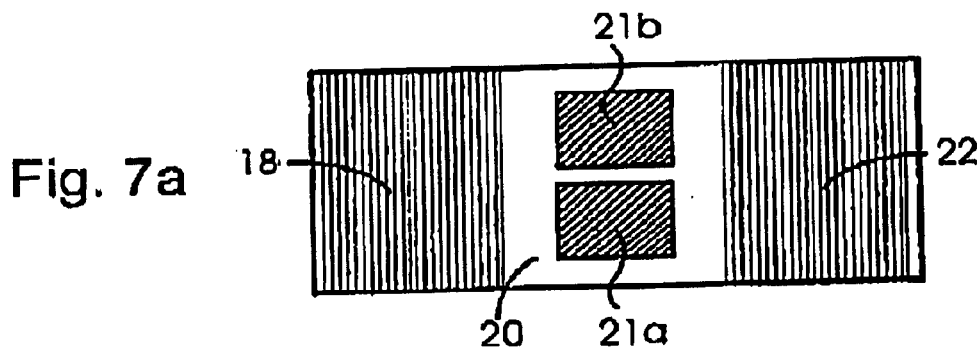
FIG. 7 is a schematic top view illustration of the embodiment of present invention as shown in FIG. 6 with a) one sensor chip unit and b) the corresponding optical transducer unit. In c) and d), an array of two sensor chip units and two optical transducer units, respectively, are illustrated and in e) and the f), an array of four sensor chip units and four optical transducer units, respectively, are illustrated.
Figure 7B:
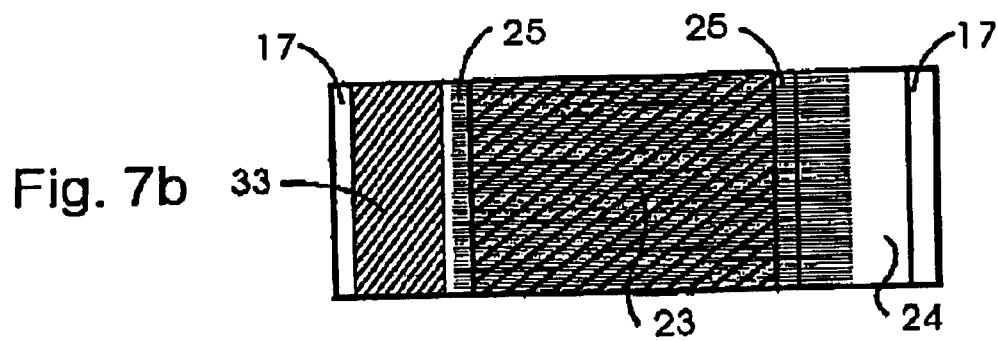
Figure 7C:
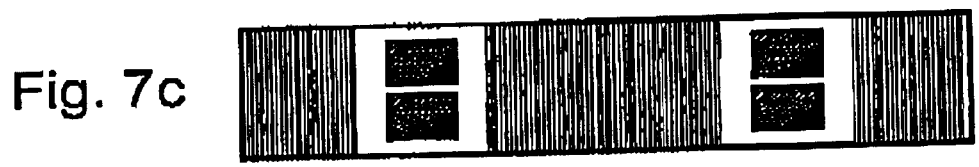
Figure 7D:
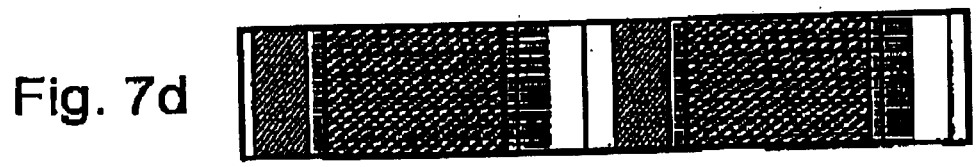
Figure 7E:
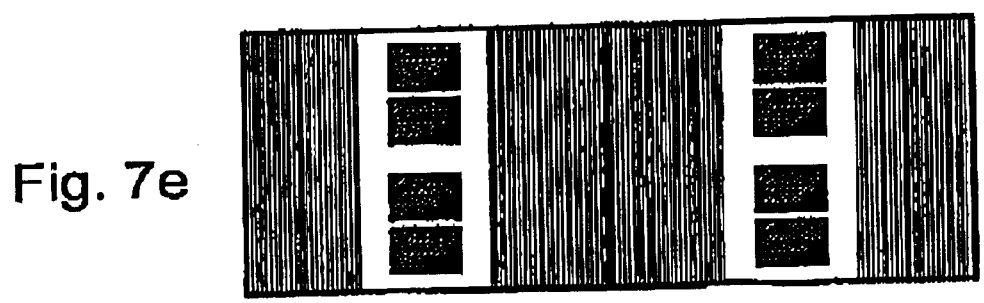
Figure 7F:
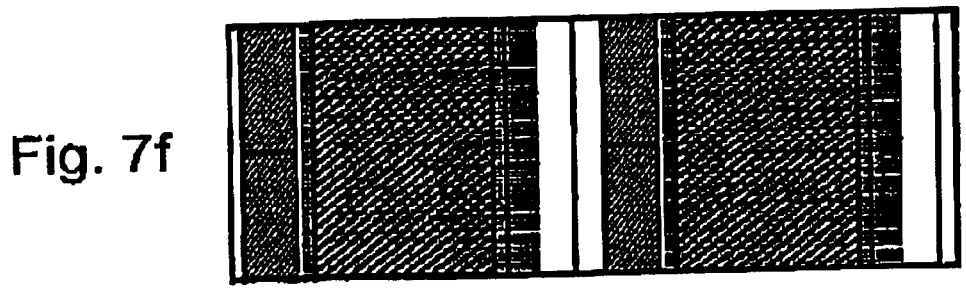

The fourth embodiment of the present invention is illustrated in FIG. 6, where the RDOEs (18) and (22) are disposed on the topside surface of the SCU (10) and the SPR sensing layer (21) is disposed on the backside surface of the SCU (10). The SCU is depicted in FIG. 2(b) and the OTU (11) in FIG. 6 is identical to the OTU (11) in FIG. 4 except that the spatial dimensions of the components and the distance between the components are different in the two configurations.

In the preferred embodiment of the present invention as illustrated in FIG. 6, a light beam from a monochromatic light source (14) mounted in a base plane (31) is collimated by a lens or a lens system (15), polarized by a polarizer (16), passes through a transparent separation plane (17) and enters the SCU (10) perpendicularly to the backside surface of the SCU. Again, a light shield (8) shields the detector array from stray light emerging from the light source (14) and prevents interference between light emitted from the light source (14) and light reflected from the surface of the detector array (23). Inside the SCU, the light beam is reflected from a RDOE (18) transforming the light beam into a cylindrically focusing light beam that is focused onto a line on a SPR metal film (20) comprising one or more sensing areas (21). The SPR metal film is disposed on the backside surface of the SCU. The focused light beam contains angular bands covering the SPR angle. After being reflected from the SPR metal film (20), the light beam is transformed into a collimated light beam by means of a second ROOE (22). The light beam exits the SCU perpendicularly to the backside surface of the SCU and reenters the OTU perpendicularly to the transparent separation plane (17). A flat mirror (24) mounted in the base plane combined with a flat mirror (25) mounted in the center of the transparent separation plane images the collimated light beam onto a detector array (23). One of the flat mirrors (25) or (24) may be replaced by a convex mirror or a RDOE with the function of diverging the light beam passing through the separation plane (17) and increasing the area on the detector array illuminated by the light beam.

FIG. 7 illustrates the construction of SPR sensors from the SCUs and OTUs as shown in FIG. 6. A schematic top view of one SCU is illustrated in FIG. 7(a) with the two sensing areas (21a) and (21b), the metal film (20) and the RDOEs (18) and (22). FIG. 7(b) shows a top-view of the corresponding OTU including the transparent separation plane (17), the mirrors (24) and (25), the detector array (23), the component (33) comprising a light source, a lens system and a polarizer. FIGS. 7(c) and 7(d) illustrate a sensor configuration comprising an array of two SCUs and the corresponding OTUs, and FIGS. 7(e) and 7(f) illustrate a sensor configuration comprising an array of four SCUs and the corresponding OTUs. The principle of constructing sensors from SCUs and OTUs can be extended to N units where N is an integer number, which can be as large as desirable. The SCUs and the OTUs can either be arranged in an array aligned in the direction parallel to the RDOEs (the top-down direction in FIG. 7) or by extending the spatial dimension of each component in this direction. The sensor can alternatively be extended combining SCUs and OTUs in the direction perpendicular to the RDOEs (the left-right direction in FIG. 7). When operating the sensor, the sensor chip should be mounted on the top of the optical transducer. A specific amount of sample comprising the analyte usually being dissolved in water is deposited on the top of the sensing areas. This is performed either using a dispenser or a flow cell mounted in the gap between the array of SCUs and the array of OTUs.

Figure 8:
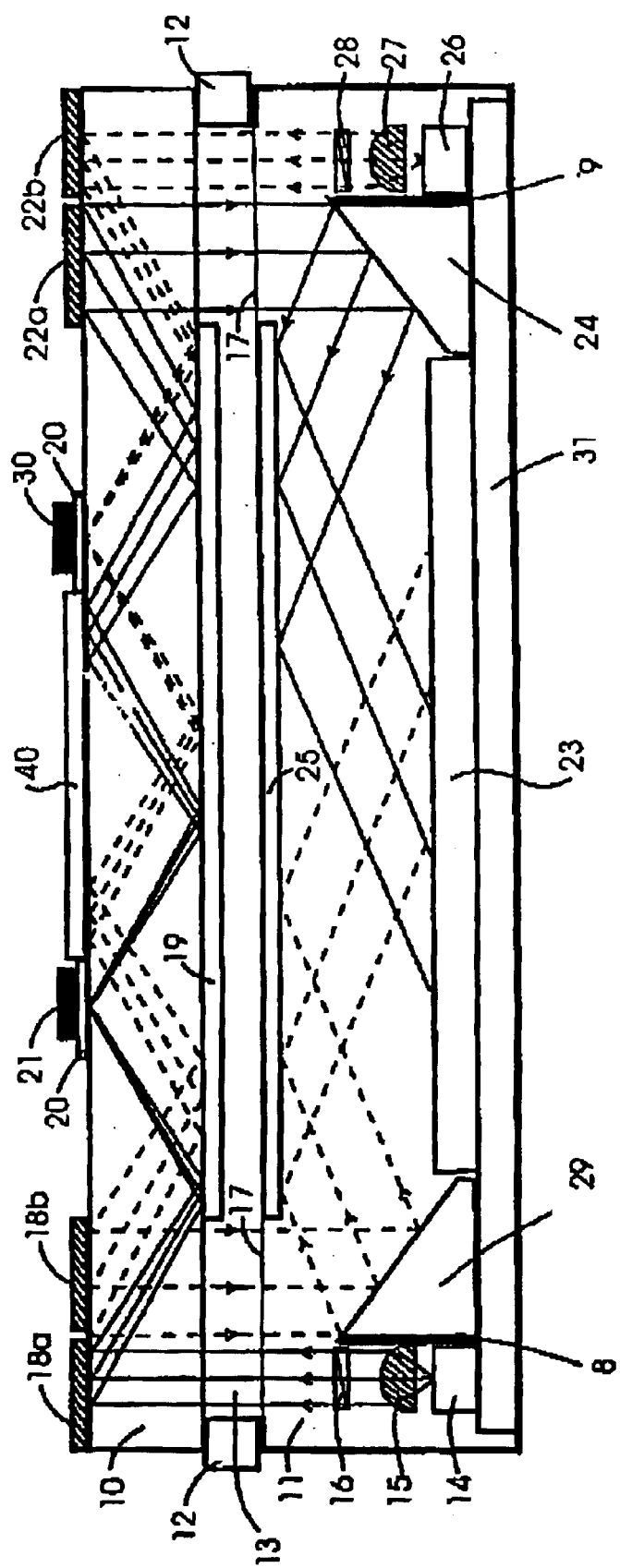
FIG. 8 is a schematic cross sectional illustration of a sensor chip unit and an optical transducer unit separated by a gap in one embodiment of the present invention based on a monochromatic light source and coupling of the light at angular bands covering the SPR angle. After being reflected from the SPR sensing area, the light rays are reflected multiple times between two flat mirrors on the backside surface and the topside surface of the sensor chip unit.

In FIG. 8, a fifth embodiment of the present invention is depicted. It comprises the same components in the SCU and in the OTU as depicted in FIG. 4, but the first light source and the second light source are now disposed symmetrically in relation to the sensing layers. In addition, the SCU comprises a plane mirror (40) on the topside surface and the OTU comprises the plane mirrors (24), (25) and (29) which serve to direct the first light beam and the second light beam towards the detector array (23). A light beam from a monochromatic light source (14) mounted in a base plane (31) is collimated by a lens or a lens system (15), polarized by a polarizer (16), passes through a transparent separation plane (17) and enters the SCU (10) perpendicularly to the backside surface of the SCU. Again, a light shield (8) shields the detector array from stray light emerging from the light source (14) and prevents interference between light emitted from the light source (14) and light reflected from the surface of the detector array (23). Inside the SCU, the light beam is reflected from a RDOE (18a) transforming the light beam into a cylindrically focusing light beam. Via a flat mirror (19) disposed on the backside surface of the SCU, the light beam is reflected and focused onto a line on a SPR metal film (20) underneath one or more sensing areas (21). The focused light beam comprises angular bands covering the SPR angle. After being reflected from the SPR metal film (20), the light beam is further reflected three times or more from alternating the flat mirror (19) and a flat mirror (40) disposed on the topside of the SCU. Via a second RDOE (22a), the light beam is transformed into a collimated light beam again, which exits the SCU perpendicularly to the backside surface of the SCU and reenters the OTU perpendicularly to the transparent separation plane (17). A mirror (24) mounted in the base plane combined with a mirror (25) mounted in the center of the transparent separation plane images the collimated light beam onto a detector array (23).

The fifth embodiment of the invention as illustrated in FIG. 8 further comprises a second monochromatic light source (26) mounted in the base plane (31) that radiates a second light beam collimated by a second lens or lens system (27), polarized by a second polarizer (28), passing through the transparent separation plane (17) and entering the SCU (10) perpendicularly to the backside surface of the SCU. A second light shield (9) shields the detector array from stray light emerging from the light source (26) and prevents interference between light emitted from the light source (26) and light reflected from the surface of the detector array (23).

Inside the SCU, the second light beam is reflected from a third RDOE (22b) transforming the second light beam into a cylindrically focusing second light beam. Via the flat mirror (19), the light beam is reflected and focused onto a line on the SPR metal film (20) underneath one or more sensing areas (21). The focused second light beam comprises angular bands covering the SPR angle.

After being reflected from the SPR metal film (20), the second light beam is further reflected three times or more from alternating the flat mirror (19) and the flat mirror (40). Via a fourth RDOE (18b), it is transformed into a collimated second light beam again, which exits the SCU perpendicularly to the backside surface of the SCU and reenters the OTU (11) perpendicularly to the transparent separation plane (17). A second flat mirror (29) mounted in the base plane (31) combined with the flat mirror (25) images the collimated second light beam onto the detector array (23). In an alternative embodiment of the present invention, one or both of the flat mirrors (24) and (29) or the flat mirror (25) are replaced by a system comprising at least one convex mirror, a convex lens or a diffractive optical element. As a result, the light beams passing through the separation plane (17) will be diverged causing an increase in the area on the detector array illuminated by the light beam. Regarding the fifth embodiment of the present invention as illustrated in FIG. 8, the sensor chips and optical transducers are constructed from SCUs and OTUs in a similar manner as the embodiment of the invention illustrated in FIGS. 4(b) and 5.

Before exiting the SCU, the light beams in the configuration depicted in FIG. 8 are reflected at a larger number of surfaces and travels a longer path length than the light beam in the configuration depicted in FIG. 4(b). Since the light beam entering the sensor chip in FIG. 8 is reflected twice before impinging on the SPR film and it is reflected four times after being reflected from the SPR film, the width of the beam is enlarged by a factor of 2. For the same pixel size of the detector array, a larger beam diameter implies that a better resolution can be obtained in the detector array, but at the expense of a larger SCU and OTU. Extending the length of the region between the sensing areas (21) and (30) and thereby incorporating more reflections between the plane mirrors (19) and (40), the width of the light beam w at the output of the SCU can be increased according to: w=(k+1)$w_0$/2. In this expression, $w_0$ is the width of the light beam entering the SCU and k is the number of reflections for the light beam from the mirrors (19) and (40). The reflections are counted from the first reflection after the reflection from the SPR metal film and prior to the reflection from the RDOE, which is (22b) for the first light beam and (18b) for the second light beam. For the configuration in FIG. 4(b), k=1 and w=$w_0$ and for the configuration in FIG. 8, k=3 and w=2$w_0$.

Figure 9A:
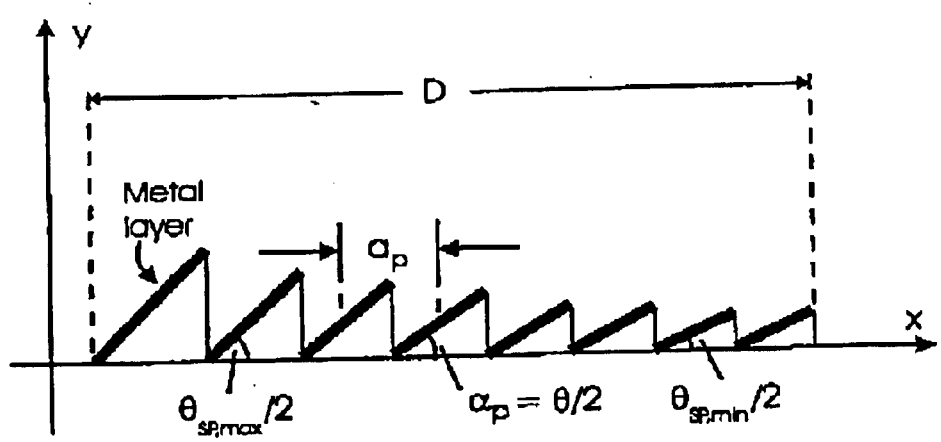
FIG. 9(a) illustrates an example of a reflective diffractive optical element (RDOE) as employed in the present invention having an aperture D, a grating distance $a_p$ and a grating angle $\alpha_p$ for the p'th grating element.

FIGS. 9(a) and (b) illustrate a design example of a RDOE as employed in the present invention with two modes of operation. In mode 1 [see (18a) in FIG. 3(a)], the RDOE reflects a collimated and perpendicularly incident light beam at angular bands covering the SPR angle ($\theta_{SP}$). In mode 2 [see (22a) in FIG. 3(a)], the RDOE reflects a light beam diverging from the SPR metal film and converts it into a collimated light beam exiting the SCU perpendicularly to the backside surface of the SCU.

Figure 9B:
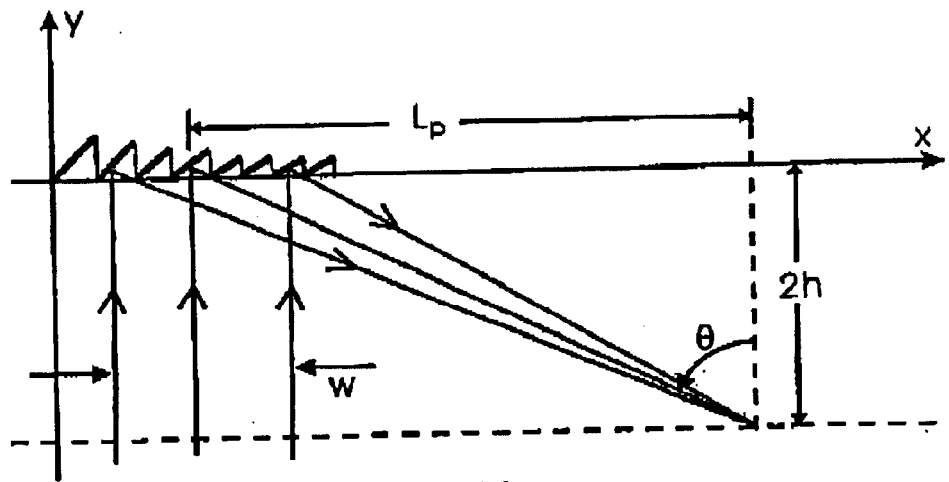
FIG. 9(b) illustrates collimated light rays being reflected to light rays and converging to a focal point at one side of the RDOE in (a).
Figure 9C:
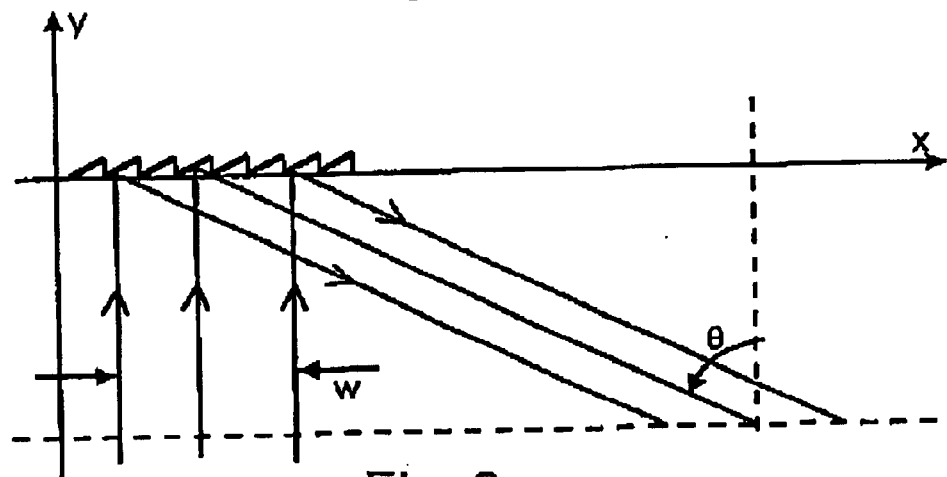
FIG. 9(c) illustrates another example of a RDOE, where collimated light rays are reflected to light rays collimated at one side of the RDOE.

The dimensions of the RDOE are depicted in FIG. 9(a), where D is an aperture D, $a_p$ is a grating distance and $\alpha_p$ is a grating angle for the p'th grating element. The corresponding transformation of the incident collimated light rays to light rays converging to a focal point is illustrated in FIG. 9(b) for the case of mode 1. The design of the RDOE for the case of mode 2 is the mirror image of the design in FIG. 9(a) in a plane parallel to the plane of incidence and positioned at the focal point. FIG. 9(c) illustrates another design example of a RDOE as employed in the embodiment of the invention as depicted in FIG. 4(a), where collimated light rays are reflected to light rays collimated at one side of the RDOE.

Figure 10A:
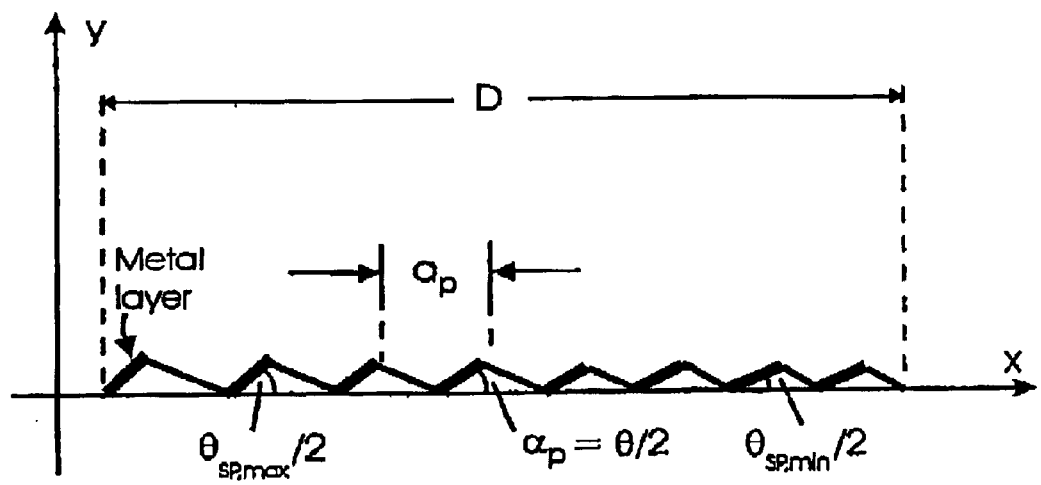
FIG. 10(a) shows an alternative configuration of the RDOE as employed in the present invention having an aperture D, a grating distance $a_p$, a grating angle $\alpha_p$ and a second grating angle $\beta_p$ for the p'th grating element.

FIGS. 10(a), (b) and (c) illustrate an alternative design example of a RDOE, where D is an aperture, $a_p$ is a grating distance, $\alpha_p=\theta/2$ is a grating angle and $\beta_p=90°-\theta$ is a second grating angle for the p'th grating element. The function of this grating is the same as in FIG. 9, but the configuration employs a second grating angle rather than vertical grating walls.

The RDOEs can be made using various processing techniques in transparent materials for the wavelength of light like polymers (e.g. polycarbonate, polystyrene, polyetherimide or polyurethane resin), glass (e.g. SF2, SF5, SF11 or sapphire) or silicon and combining them with metal evaporation or sputtering. Plastic usually exhibits birefringence, but the polarization of the light beam can be tuned to match the TM mode of the surface plasmon by means of a polarizer. The possible processing techniques includes one-level gray-tone lithography, diamond turning, photolithographic binary optics, e-beam writing, laser micromechanical etching, and analogue or digital holographic writing in photoresist. The processing techniques can be employed either directly in processing the sensor chip or in the fabrication of a mould for the sensor chip.

The metal film on the top of the RDOEs can be gold, silver, aluminum, titanium or the like. A metal layer thickness of about 200 nm (or greater) generally provides sufficient reflectivity, and a metal thickness in excess of 100 nm generally will not support an SP wave.

The SPR metal film thickness is typically ~50 nm. Gold or silver will be used for the wavelength range 400–1000 nm. In the infrared, materials like aluminum, copper and tantalum may also be employed. The thickness and compositions of the SPR metal films and the RDOE metal films are different. The fabrication of these films can be accomplished using masks (e.g. metal masks or photolithographic masks) during evaporation or sputtering of the metals.

Figure 10B:
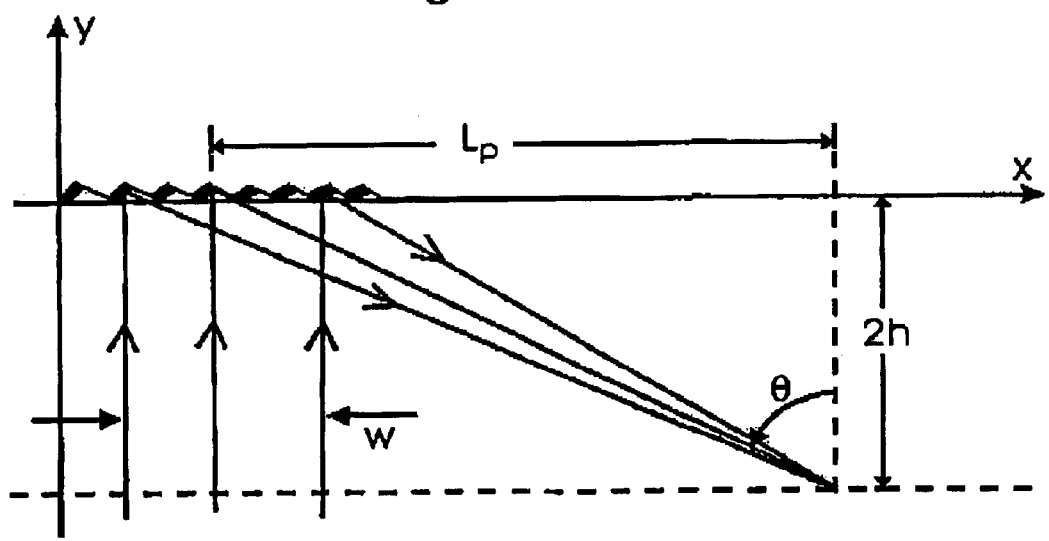
FIG. 10(b) illustrates collimated light rays being reflected to light rays and converging to a focal point at one side of the RDOE in (a).

In FIGS. 9(b) and 10(b), the angular bands of $\theta$ for the light coupling to the SP vary from $\theta_{min}$ to $\theta_{max}$. The corresponding grating angle for the p'th grating element is $\alpha_p=\theta/2$, where p=0 is the first element and p=N is the last element in the grating. Assuming that the grating periodicity is much larger than the wavelength of light, the grating period can be estimated from the following formula based on the diffraction condition that rays diffracted from each p grating element interfere constructively;

$$a_p = \frac{m\lambda}{n_g L_p} 2h\left[1+\left(\frac{L_p}{2h}\right)^2\right]^{1/2} \quad (3)$$

where $\lambda$ is the wavelength of light, m is the diffraction order, $L_p$ and 2 h are the horizontal and vertical distances between the focal point of the grating and the position of the p'th grating element, respectively [see FIGS. 9(b) and 10(b)].

Figure 10C:
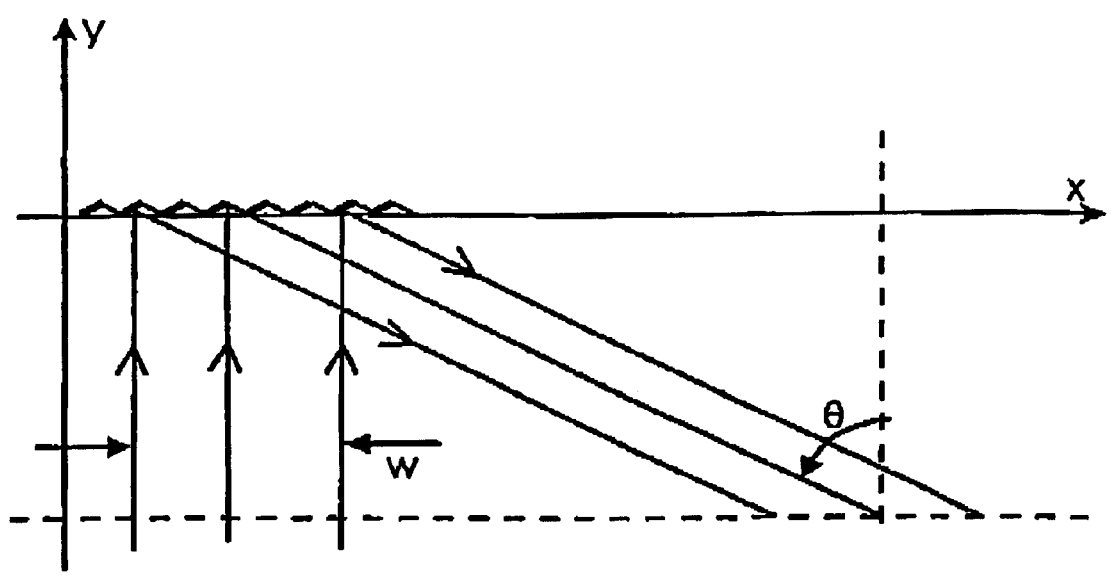
FIG. 10(c) illustrates another example of a RDOE, where collimated light rays are reflected to light rays collimated at one side of the RDOE.

As an example, assuming that the beam width is w=2 mm with $L_{p=0}$=8 mm and $L_{p=N}$=6 mm, h=2 mm, $\lambda/n_g$=0.5 $\mu$m and m=10, then $a_0$=5.6 $\mu$m and $a_N$=6.0 $\mu$m. For the case of FIG. 9, the depth of the grating $d_p$~3 $\mu$m, whilst $d_p$~1.4 $\mu$m for the case of FIG. 10. In the present example, the grating period $a_p$~6 $\mu$m is much larger than the wavelength of light/$n_g$~0.5 $\mu$m. It is also possible to employ gratings where the grating period is comparable to or much smaller than the wavelength of light.

The incident light beam is collimated in FIG. 9(b) and each diffraction element of the RDOE images the light on the same focal point. If D is sufficiently broader than w, a lateral displacement of the sensor chip relative to the optical transducer results in a change of the angle $\theta$ for coupling to the SP waves. This fact can be utilized to make a coarse adjustment of $\theta$ for the embodiments of the present invention as depicted in FIGS. 2 and 6. The lateral displacement (see arrows in FIGS. 2 and 6) can be performed by means of manual or motorized micrometer drives. It implies that a SCU can be used to cover a broad range of SPR angles and a large dynamic range in refractive index. As an alternative to focusing a light beam on the SPR metal film at angular bands covering the SPR angle, the lateral displacement may also be utilized in scanning the angle of incidence of a light beam on the SPR metal film. In this configuration, w of the light beam should be less than 1/20 of D. In alternative configurations, the RDOEs can be designed as an array of elements, where each element as illustrated in FIG. 9(b) focuses an incident collimated light beam to a focal point on the SPR metal film at angular bands covering the SPR angle. As a result, a lateral displacement of the sensor chip relative to the optical transducer causes a corresponding lateral movement of the focal point incident on the SPR metal film. Employing this method, the sensing areas can be disposed in a two-dimensional array. The sensor chips can be mounted on a rotatory disc and the lateral displacement (see arrows in FIGS. 3 and 6) can be performed by means of a motor of the type used in compact disc players.

Depending on parameters including the metal film thickness, the angular bands covered by the SPR has typically a full width half maximum (FWHM) in the reflectivity vs. angular spectrum of $\Delta\theta \sim 1°-3°$. In order to obtain a narrow SPR signal, the optimum thickness of the SPR metal film is determined empirically for a specific sensor and it is typically in the range 30–50 nm. It is determined by the complex dielectric function of the metal $\epsilon_m = \epsilon_{mr} + i\epsilon_{mi}$, where according to the Drude formula:

$$\varepsilon_{mr} = 1 - \frac{\lambda^2 \lambda_c^2}{\lambda_p^2 (\lambda_c^2 - \lambda^2)}; \quad \varepsilon_{mi} = \frac{\lambda^2 \lambda_c^2}{\lambda_p^2 (\lambda_c^2 - \lambda^2)}; \quad (4)$$

where $\epsilon_{mr}$ and $\epsilon_{mi}$ are the real part and imaginary part of the dielectric function, respectively, $\lambda_p$ is the plasma wavelength and $\lambda_c$ is the collision wavelength.

As an example, employing gold as the SPR metal film, we obtain from Eq. (4); $\epsilon_{mr} = -20.7$ and $\epsilon_{mi} = 1.89$. Since $|\epsilon_{mi}| \ll |\epsilon_{mr}|$ the following expression can be used in the calculation of $\theta_{SP}$:

$$n_g \sin\theta_{sp} \cong \left[ \frac{\varepsilon_{mr} n_s^2}{\varepsilon_{mr} + n_s^2} \right]^{\frac{1}{2}} \quad (5)$$

where $n_s$ is the refractive index of the sample to be measured (i.e. the sensing areas) and $n_g$ is the refractive index of the sensor chip.

As an example, assuming that the sensing areas are based on MREs immobilized in a polymer membrane with $n_s \sim 1.46$ and the sensor chip is made of a high refractive index plastic ($n_g \sim 1.66$), the SPR angle becomes according to Eq. (5); $\theta_{SP} \sim 68°$. As observed from Eq. (5), $\theta_{SP}$ depends strongly on the refractive index of the sensor chip material and the membrane. Usually, $\theta_{SP}$ is in the angular range 50°–80°. The value of $\theta_{SP}$ can be lowered to the critical angle for total reflection between the substrate and the sensing area employing a few hundreds nanometers thick intermediate layer of a dielectric with a refractive index lower than $n_g$ and disposed in between the substrate and the metal layer. The dielectric layer results in the excitation of a long-range SP with a narrower $\Delta\theta$, but with a broader lateral spatial extension of approximately 300 µm compared to 10 µm for a normal (short range) SP. Possible materials for the intermediate layer are $MgF_2$, $CaF_2$, $AlF_3$, $BaF_2$ and $Na_5Al_3F_{14}$.

Since the RDOEs focus a light beam onto a line on the SPR metal layer, two or more sensing areas can be illuminated. For example, if the light beam width is 1 mm and each sensing area has a diameter of 200 µm with a spacing of 50 µm, a sensing area with 4 elements is illuminated by one light beam. One of the sensing areas acts as a reference, which is responsive to unspecific changes due to effects from temperature, pressure, ageing, analyte refractive index, membrane swelling and other disturbances in the environment. The other sensing areas on the top of the SPR metal film can be based on MREs immobilized in membranes with a thickness ~0.3 µm–1 µm deposited on the top the SPR metal layer. The possible membrane compounds include hydrogel, for example, polysaccharide such as, e.g. agarose, dextran, carrageenan, alginic acid, starch, cellulose or derivatives thereof such as, for example, carboxymethyl derivatives or an organic polymer such as e.g. poly (vinylalcohol), poly(vinylchloride), polyacrylic acid, polyacrylamide and polyethylene glycol.

The MREs are for example ionophores and chromoionophores either immobilized via hydrophobic forces in a lipophilic polymer membrane or copolymerized in the polymer membrane. An ionophore acts as a selective recognition element for a particular ionic or neutral ionogenic chemical compound (i.e. the analyte). In order to maintain electrical neutrality inside the polymer membrane phase, the binding of the analyte by the ionophore is coupled with the coextraction or ion exchange of a second ionic species (usually a proton) giving rise to a change in the absorption coefficient ($\Delta\alpha$) of the chromoionophore. The corresponding change in the refractive index ($\Delta n$) of the membrane as given by the Kramers-Kronig transform causes a change in the SPR signal through $n_s$ in Eq. (5). When the operating wavelength is about 100 nm longer than the position of the maximum $\Delta\alpha$, a large and wavelength insensitive $\Delta n$ can be achieved at a small $\Delta\alpha$. Operating close to the maximum in $\Delta\alpha$ results in a more sensitive SPR response where information of both $\Delta\alpha$ and $\Delta n$ can be determined from the response. For a typical chromoionophore like ETH 5294, maximum in $\Delta\alpha$ occurs in the wavelength range 500 to 700 nm. A suitable wavelength of light is then 670–850 nm, where a number of commercial semiconductor lasers and light emitting diodes provide light emission.

Other possible MREs are antibodies/antigens and the present SPR sensor could be employed as a label-free immunosensor based on antibodylantigen reactions to determine specific analytes. Antibodies can readily be immobilized in a hydrogel through covalent binding. The Biosensor group from BIAcore has used antibodies immobilized in a carboxymethyl-dextran hydrogel membrane on the gold film of a SPR sensor for detecting various biological compounds. An alternative to antibody/antigen reactions is the utilization of molecular imprinting techniques, where synthetic polymers possess selective molecular recognition properties. This is due to the self-assembled or preorganized positioning of functional groups which generate recognition sites within a polymer membrane that are complementary to the shape and the functional groups of the analyte. A second alternative is the use of oligonucleotide ligands, which may provide specific and high affinity binding with specific analytes.

Another application of the present invention is in the DNA hybridization analysis. On sensor-chips, large arrays of oligonucleotides or probes originating from cDNA libraries can be fabricated employing for example light directed synthesis or high-speed robotic printing techniques. Depending on applications, such arrays constitute from a few tenth of probes to $\sim 10^6$ probes/cm$^2$.

Traditionally, the detection scheme is performed by use of fluorescent labeling and detecting the hybridization pattern of target DNA using a scanning confocal optical microscope. According to the present invention, the hybridization reaction of a large number of sensing areas (in this case the probe areas) can be detected monitoring the shift in the SPR curve for each sensing area.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A surface plasmon resonance sensor comprising a first unit and a second unit, said first and second units being separable, and wherein said first unit comprises:
   a first housing,
   a film of electrically conducting material being adapted to support surface plasmons, said film being held by a first exterior surface part of the first housing,
   optical input means positioned on a second exterior surface part of the first housing so as to receive an optical light beam from the second unit,
   optical output means positioned on a third exterior surface part of the first housing so as to transmit an optical light beam to the second unit,
   a first set of optical elements being adapted to direct the received optical light beam from the first unit towards the electrically conducting film,
   a second set of optical elements being adapted to direct an optical light beam from the electrically conducting film towards the optical output means so as to transmit the optical light beam from the electrically conducting film to the second unit,
   and wherein said second unit comprises;
   a second housing
   means for emitting an optical light beam,
   a first set of optical elements being adapted to prepare the emitted optical light beam,
   optical output means positioned on a first exterior surface part of the second housing so as to transmit the prepared optical light beam to the first unit,
   optical input means positioned on a second exterior surface part of the second housing so as to receive an optical light beam from the first unit,
   detecting means being adapted to detect the optical light beam received from the first unit,
   a second set of optical elements being adapted to direct the received optical light beam from the first unit towards the detecting means,
   wherein the propagation directions of the optical light beams at the positions of the optical input and optical output means are essentially perpendicular to the exterior surface parts of the first and the second housing so as to avoid refraction of the optical light beams upon entry of said optical light beams into the first and second unit.

2. A surface plasmon resonance sensor according to claim 1, wherein the emitting means comprises a laser source, such as a semiconductor laser diode.

3. A surface plasmon resonance sensor according to claim 1, wherein the emitting means comprises a light source emitting light at essentially a single wavelength.

4. A surface plasmon resonance sensor according to claim 1, wherein the emitting means comprises a light source emitting light at a plurality of wavelengths, such as a light emitting diode.

5. A surface plasmon resonance sensor according to claim 1, wherein the first set of optical elements of the second unit comprises means for collimating the emitted optical light beam.

6. A surface plasmon resonance sensor according to claim 5, wherein the first set of optical elements of the second unit further comprises means for polarizing the emitted optical light beam.

7. A surface plasmon resonance sensor according to claim 1, wherein the input and output means of the first and second units comprise antireflecting coatings.

8. A surface plasmon resonance sensor according to claim 1, wherein the detecting means comprises an array of photosensitive elements, such as a multiple photo detector array, a charge coupled device or a complementary metal oxide semiconductor image sensor.

9. A surface plasmon resonance sensor according to claim 1 further comprising a light shield member.

10. A surface plasmon resonance sensor according to claim 1, wherein the first set of optical elements of the first unit comprises a diffractive member, such as a diffractive grating or a holographic grating, said diffractive member being adapted to transform a collimated optical light beam into a focused optical light beam.

11. A surface plasmon resonance sensor according to claim 1, wherein the second set of optical elements of the first unit comprises a diffractive member, such as a diffractive grating or a holographic grating, said diffractive member being adapted to transform a diverging optical light beam into a collimated optical light beam.

12. A surface plasmon resonance sensor according to claim 1, wherein the first set of optical elements of the first unit comprises a reflective member, such as a diffractive grating or a holographic grating, said reflective member being adapted to transform a collimated optical light beam into a focused optical light beam.

13. A surface plasmon resonance sensor according to claim 1, wherein the second set of optical elements of the first unit comprises a reflective member, such as a diffractive grating or a holographic grating, said reflective member being adapted to transform a diverging optical light beam into a collimated optical light beam.

14. A surface plasmon resonance sensor according to claim 1, wherein the second set of optical elements comprises a reflective member, such as a reflective mirror.

15. A surface plasmon resonance sensor according to claim 1, wherein the electrically conducting film is a metal film, such as a gold film, a silver film, an aluminum film or a titanium film.

16. A surface plasmon resonance sensor according to claim 15, wherein the electrically conducting film comprises a plurality of electrically conducting films, said plurality of films being arranged in a laterally extending pattern.

17. A surface plasmon resonance sensor according to claim 1 further comprising a layer of dielectric material being positioned between the electrically conducting film and the first exterior surface part of the first housing.

18. A surface plasmon resonance sensor according to claim 16 further comprising a layer of dielectric material being positioned between each of the plurality of electrically conducting films and the first exterior surface part of the first housing.

19. A surface plasmon resonance sensor according to claim 1 further comprising moving means, said moving means being adapted to move the first and second unit relative to each other so as to move the focus point of an optical light beam relative to an electrically conducting film.

20. A surface plasmon resonance sensor according to claim 1 further comprising moving means, said moving means being adapted to move the first and second unit relative to each other so as to vary the angle of incidence of an optical light beam directed towards an electrically conducting film.

21. A surface plasmon resonance sensor comprising in combination two or more surface plasmon resonance sensors according to claim 1, said combination of two or more surface plasmon resonance sensors being arranged in a laterally extending pattern.

22. A method of determining the bio-/chemical composition of a sample using a surface plasmon resonance sensor, said surface plasmon resonance sensor comprising a first unit and a second unit, said first and second units being separable, and wherein said first unit comprises:
  a first housing,
  a film of electrically conducting material being adapted to support surface plasmons, said film being held by a first exterior surface part of the first housing,
  optical input means positioned on a second exterior surface part of the first housing so as to receive an optical light beam from the second unit,
  optical output means positioned on a third exterior surface part of the first housing so as to transmit an optical light beam to the second unit,
  a first set of optical elements being adapted to direct the received optical light beam from the first unit towards the electrically conducting film,
  a second set of optical elements being adapted to direct an optical light beam from the electrically conducting film towards the optical output means so as to transmit the optical light beam from the electrically conducting film to the second unit,
and wherein said second unit comprises:
  a second housing,
  means for emitting an optical light beam,
  a first set of optical elements being adapted to prepare the emitted optical light beam,
  optical output means positioned on a first exterior surface part of the second housing so as to transmit the prepared optical light beam to the first unit,
  optical input means positioned on a second exterior surface part of the second housing so as to receive an optical light beam from the first unit,
  detecting means being adapted to detect the optical light beam received from the first unit,
  a second set of optical elements being adapted to direct the received optical light beam from the first unit towards the detecting means,
  the method comprising the steps of:
    emitting an optical light beam,
    preparing the emitted optical light beam by means of the first set of optical elements,
    transmitting the prepared optical light beam from the second unit to the first unit in such a way that the propagation direction of the optical light beam at the position of the optical input means is essentially perpendicular to the first exterior surface part of the second housing and to the second exterior surface part of the first housing so as to avoid refraction of the optical light beam upon entry into the first unit,
    directing the optical light beam towards the electrically conducting film by means of the first set of optical elements,
    directing the optical light beam from the electrically conducting film towards the optical output means,
    transmitting the optical light beam from the first unit the second unit in such a way that the propagation direction of the optical light beam at the position of the optical output means is essentially perpendicular to the third exterior surface part of the first housing and to the second exterior surface part of the second housing so as to avoid refraction of the optical light beam upon entry into the second unit,
    directing the optical light beam towards the detecting means,
    detecting the optical light beam received from the first unit.

23. A surface plasmon resonance sensor comprising a first unit, said first unit comprising:
  a first housing,
  a layer of electrically conducting material being adapted to support surface plasmons, said layer being held by a first exterior surface part of the first housing,
  optical input means positioned on a second exterior surface part of the first housing, said optical input means being adapted to receive an optical light beam,
  optical output means positioned on a third exterior surface part of the first housing, said optical output means being adapted to transmit an optical light beam,
  a first diffractive optical element being adapted to direct the received optical light beam towards the electrically conducting layer,
  a second diffractive optical element being adapted to direct a reflected optical light beam from the electrically conducting layer towards the optical output means,
  wherein the propagation directions of the optical light beams at the positions of the optical input and optical output means are essentially perpendicular to the exterior surface parts of the first housing so as to avoid refraction of the optical light beams at the positions of the optical input and optical output means.

24. A surface plasmon resonance sensor according to claim 23 further comprising a second unit, said second unit comprising:
  a second housing,
  means for emitting an optical light beam,
  a set of optical elements being adapted to prepare the emitted optical light beam,
  optical output means positioned on a first exterior surface part of the second housing, said optical output means being adapted to transmit the prepared optical light beam to the first unit,
  optical input means positioned on a second exterior surface part of the second housing, said optical input means being adapted to receive an optical light beam from the first unit,
  detecting means being adapted to detect the received optical light beam from the first unit,
  wherein the propagation directions of the optical light beams at the positions of the optical input and optical output means are essentially perpendicular to the exterior surface parts of the second housing so as to avoid refraction of the optical light beams at the positions of the optical input and optical output means.

25. A surface plasmon resonance sensor according to claim 24, wherein the second unit further comprises an optical element being adapted to direct the received optical light beam from the first unit towards the detecting means.

26. A surface plasmon resonance sensor according to claim 24, wherein the light emitting means comprises a laser source, such as a semiconductor laser diode.

27. A surface plasmon resonance sensor according to claim 24, wherein the light emitting means comprises a light source emitting light at essentially a single wavelength.

28. A surface plasmon resonance sensor according to claim 24, wherein the light emitting means comprises a light source emitting light at a plurality of wavelengths, such as a light emitting diode.

29. A surface plasmon resonance sensor according to claim 24, wherein the set of optical elements of the second unit comprises means for collimating the emitted optical light beam.

30. A surface plasmon resonance sensor according to claim 29, wherein the set of optical elements of the second unit further comprises means for polarizing the emitted optical light beam.

31. A surface plasmon resonance sensor according to claim 24, wherein the input and output means of the first and second units comprise antireflecting coatings.

32. A surface plasmon resonance sensor according to claim 24, wherein the detecting means comprises an array of photosensitive elements, such as a multiple photo detector array, a charge coupled device or a complementary metal oxide semiconductor image sensor.

33. A surface plasmon resonance sensor according to claim 23, wherein the first and second diffractive optical element of the first unit comprises an optical grating, such as a reflective holographic grating.

34. A surface plasmon resonance sensor according to claim 23, wherein the electrically conducting layer is a metal film, such as a gold film, a silver film, an aluminum film or a titanium film.

35. A surface plasmon resonance sensor according to claim 23, wherein the electrically conducting layer comprises a plurality of electrically conducting layers, said plurality of layers being arranged in a laterally extending pattern.

36. A surface plasmon resonance sensor according to claim 23 further comprising a layer of dielectric material positioned between the electrically conducting layer and the first exterior surface part of the first housing.

37. A surface plasmon resonance sensor according to claim 35 further comprising a layer of dielectric material positioned between each of the plurality of electrically conducting layers and the first exterior surface part of the first housing.

38. A surface plasmon resonance sensor according to claim 23 further comprising moving means, said moving means being adapted to move the first and second unit relative to each other so as to move the focus point of the optical light beam relative to one or more of the electrically conducting layers.

39. A surface plasmon resonance sensor according to claim 23 further comprising moving means, said moving means being adapted to move the first and second unit relative to each other so as to vary the angle of incidence of an optical light beam directed towards to one or more of the electrically conducting layers.

40. A surface plasmon resonance sensor comprising:
a transparent member,
a layer of electrically conducting material being adapted to support surface plasmons, said layer being held by an exterior surface part of the member,
a first optical grating being held by a first exterior surface part of the member and being adapted to direct a received optical light beam towards the electrically conducting layer, wherein the propagation direction of the received optical light beam at the position of the first optical grating is essentially perpendicular to the first exterior surface part of the member and wherein the received optical light beam is substantially collimated, and
a second optical grating being held by a second exterior surface part of the member and being adapted to receive an optical light beam from the electrically conducting layer and being adapted to re-emit the optical light beam received from the electrically conducting layer, wherein the propagation direction of the re-emitted optical light beam at the position of the second optical grating is essentially perpendicular to the second exterior surface part of the member and wherein the re-emitted optical light beam is substantially collimated.

41. A surface plasmon resonance sensor according to claim 40 further comprising
means for emitting an optical light beam,
a set of optical elements being adapted to prepare the emitted optical light beam, and
means for detecting the re-emitted optical light beam.

42. A surface plasmon resonance sensor according to claim 41 further comprising an optical element being adapted to direct the re-emitted optical light beam towards the detecting means.

43. A surface plasmon resonance sensor according to claim 41, wherein the light emitting means comprises a laser source, such as a semiconductor laser diode.

44. A surface plasmon resonance sensor according to claims 41, wherein the light emitting means comprises a light source emitting light at essentially a single wavelength.

45. A surface plasmon resonance sensor according to claim 41, wherein the light emitting means comprises a light source emitting light at a plurality of wavelengths, such as a light emitting diode.

46. A surface plasmon resonance sensor according to claim 41, wherein the set of optical elements comprises means for collimating the emitted optical light beam.

47. A surface plasmon resonance sensor according to claim 46, wherein the set of optical elements further comprises means for polarizing the emitted optical light beam.

48. A surface plasmon resonance sensor according to claim 41, wherein the detecting means comprises an array of photosensitive elements, such as a multiple photo detector array, a charge coupled device or a complementary metal oxide semiconductor image sensor.

49. A surface plasmon resonance sensor according to claim 40, wherein the electrically conducting layer is a metal film, such as a gold film, a silver film, an aluminum film or a titanium film.

* * * * *